United States Patent
Nock

(10) Patent No.: US 12,402,978 B2
(45) Date of Patent: Sep. 2, 2025

(54) MARKER DELIVERY DEVICE WITH PUSH ROD HAVING ACTUATION FEATURES

(71) Applicant: Devicor Medical Products, Inc., Cincinnati, OH (US)

(72) Inventor: Andrew P. Nock, Dayton, OH (US)

(73) Assignee: Devicor Medical Products, Inc., Cincinnati, OH (US)

( * ) Notice: Subject to any disclaimer, the term of this patent is extended or adjusted under 35 U.S.C. 154(b) by 433 days.

(21) Appl. No.: 17/863,813

(22) Filed: Jul. 13, 2022

(65) Prior Publication Data

US 2022/0346907 A1    Nov. 3, 2022

Related U.S. Application Data

(63) Continuation of application No. PCT/US2021/013352, filed on Jan. 14, 2021.

(60) Provisional application No. 62/961,367, filed on Jan. 15, 2020.

(51) Int. Cl.
*A61B 90/00* (2016.01)

(52) U.S. Cl.
CPC ...... *A61B 90/39* (2016.02); *A61B 2090/3987* (2016.02)

(58) Field of Classification Search
CPC .................................................. A61B 90/39
See application file for complete search history.

(56) References Cited

U.S. PATENT DOCUMENTS

| | | | |
|---|---|---|---|
| 2,883,984 A * | 4/1959 | Candido, Jr. | A61M 37/0069 604/61 |
| 6,083,524 A | 7/2000 | Sawhney et al. | |
| 6,162,241 A | 12/2000 | Coury et al. | |
| 6,270,464 B1 | 8/2001 | Fulton, III et al. | |
| 6,356,782 B1 | 3/2002 | Sirimanne et al. | |
| 6,605,294 B2 | 8/2003 | Sawhney | |
| 8,600,481 B2 | 12/2013 | Sirimanne et al. | |
| 8,939,910 B2 | 1/2015 | Fisher | |
| 9,592,110 B1 | 3/2017 | Dan et al. | |
| 11,179,141 B2 | 11/2021 | Mescher et al. | |
| 2007/0142725 A1 * | 6/2007 | Hardin | A61B 90/39 600/431 |
| 2016/0166817 A1 * | 6/2016 | Vetter | A61B 17/3468 604/181 |

(Continued)

FOREIGN PATENT DOCUMENTS

| | | |
|---|---|---|
| EP | 1836979 B1 | 5/2012 |
| EP | 2719355 A2 | 5/2014 |
| WO | 2007/069105 A2 | 6/2007 |

(Continued)

OTHER PUBLICATIONS

International Search Report and Written Opinion dated Dec. 7, 2021 for Application No. PCT/US2021/013352, 18 pages.

*Primary Examiner* — Chao Sheng
(74) *Attorney, Agent, or Firm* — Frost Brown Todd LLP

(57) ABSTRACT

A marker delivery device includes a housing, a flexible push rod, and a wheel. The push rod includes a first transverse dive surface and a deployer tip. The deployer tip is configured to receive a biopsy site marker. The wheel includes a second transverse drive surface. The first transverse drive surface is configured to be driven by the second transverse drive surface to translate the push rod distally.

19 Claims, 28 Drawing Sheets

(56) References Cited

U.S. PATENT DOCUMENTS

2016/0278984 A1* 9/2016 Loushin ................ A61F 11/202

FOREIGN PATENT DOCUMENTS

| WO | 2012/010783 | A1 | 1/2012 |
| WO | 2014/111911 | A1 | 7/2014 |
| WO | 2016/044226 | A2 | 3/2016 |

* cited by examiner

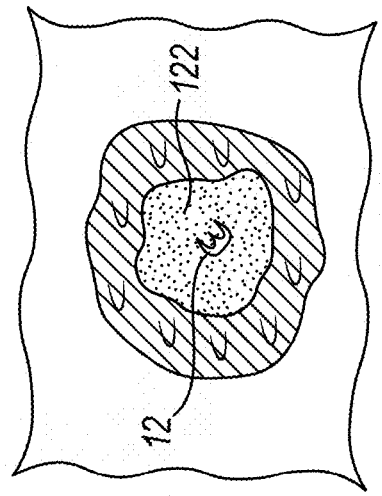
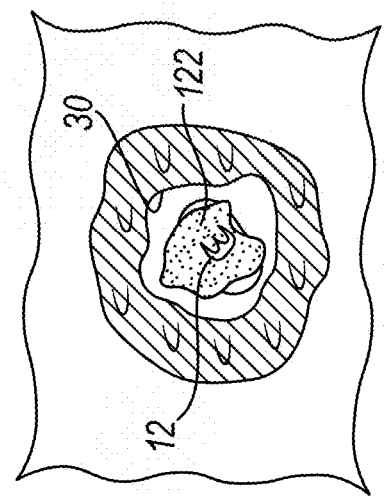
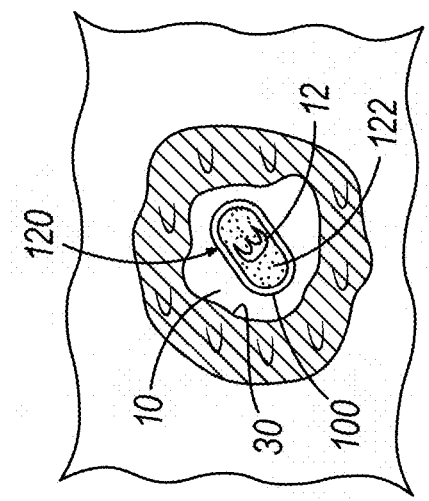

MARKER DELIVERY DEVICE WITH PUSH ROD HAVING ACTUATION FEATURES

PRIORITY

This application is a continuation of International Application No. PCT/US2021/013352, entitled "Marker Delivery Device with Push Rod Having Actuation Features," filed on Jan. 14, 2021, which claims priority to U.S. Provisional Application Ser. No. 62/961,367, entitled "Marker Delivery Device with Push Rod Having Actuation Features," filed on Jan. 15, 2020, the disclosures of which are incorporated by reference herein.

BACKGROUND

A number of patients will have breast biopsies because of irregular mammograms and palpable abnormalities. Biopsies can include surgical excisional biopsies and stereotactic and ultrasound guided needle breast biopsies. In the case of image directed biopsy, the radiologist or other physician may take a small sample of the irregular tissue for laboratory analysis. If the biopsy proves to be malignant, additional surgery (e.g., a lumpectomy or a mastectomy) may be required. In the case of needle biopsies, the patient may return to the radiologist a day or more later, and the biopsy site (the site of the lesion) may need to be relocated in preparation for the surgery. An imaging system, such as ultrasound, magnetic resonance imaging (MRI) or x-ray may be used to locate the biopsy site. In order to assist the relocation of the biopsy site, a marker may be placed at the time of the biopsy.

The use of biopsy markers are described in the following US Patents: U.S. Pat. No. 6,083,524, "Polymerizable Biodegradable Polymers Including Carbonate or Dioxanone Linkages," issued Jul. 4, 2000; U.S. Pat. No. 6,162,241, "Hemostatic Tissue Sealants," issued Dec. 4, 2000; U.S. Pat. No. 6,270,464, "Biopsy Localization Method and Device," issued Aug. 7, 2001; U.S. Pat. No. 6,356,782, "Subcutaneous Cavity Marking Device and Method," issued Mar. 12, 2002; U.S. Pat. No. 6,605,294, "Methods of Using In Situ Hydration of Hydrogel Articles for Sealing or Augmentation of Tissue or Vessels," issued Aug. 12, 2003; U.S. Pat. No. 8,600,481, "Subcutaneous Cavity Marking Device," issued Dec. 3, 2013 and U.S. Pat. No. 8,939,910, "Method for Enhancing Ultrasound Visibility of Hyperechoic Materials", issued Jan. 27, 2015. All of these US Patents are incorporated by reference in their entirety.

A biopsy site marker is used to identify a biopsy site after a biopsy procedure. Biopsy site markers are deployed through a marker delivery device that is inserted into a needle of a biopsy device. Generally, marker delivery devices have a long flexible cannula that is inserted into the needle to reach a side aperture of the needle. In some circumstances, a long flexible cannula can be cumbersome and difficult to insert into the proximal end of the needle. Thus, a need exists for a marker delivery device that reduces the overall length of the marker delivery device and helps an operator insertion of marker delivery device into the needle of a biopsy device.

These marker delivery devices can generally be configured to move a marker longitudinally through a cannula within the marker delivery device. These marker delivery devices can also generally include a ramp at the end of the cannula to change movement of the marker from a longitudinal direction to a transverse direction. The marker rides up the ramp and is expelled through the lateral aperture of the marker delivery device and the lateral aperture of the needle into tissue. This ramp may longitudinally compress the marker. This compression expands the diameter of the marker within the cannula. This compression and expansion of the marker can make it difficult to deploy a marker through the lateral aperture.

While several systems and methods have been made and used for marking tissue, it is believed that no one prior to the inventors has made or used the invention described in the appended claims.

BRIEF DESCRIPTION OF THE DRAWINGS

While the specification concludes with claims which particularly point out and distinctly claim the invention, it is believed the present invention will be better understood from the following description of certain examples taken in conjunction with the accompanying drawings, in which like reference numerals identify the same elements. In the drawings some components or portions of components are shown in phantom as depicted by broken lines.

FIGS. 1A, 1B, and 1C show exemplary aspects of placement of a biopsy site marker, in accordance with aspects of the present disclosure;

Figure 2:
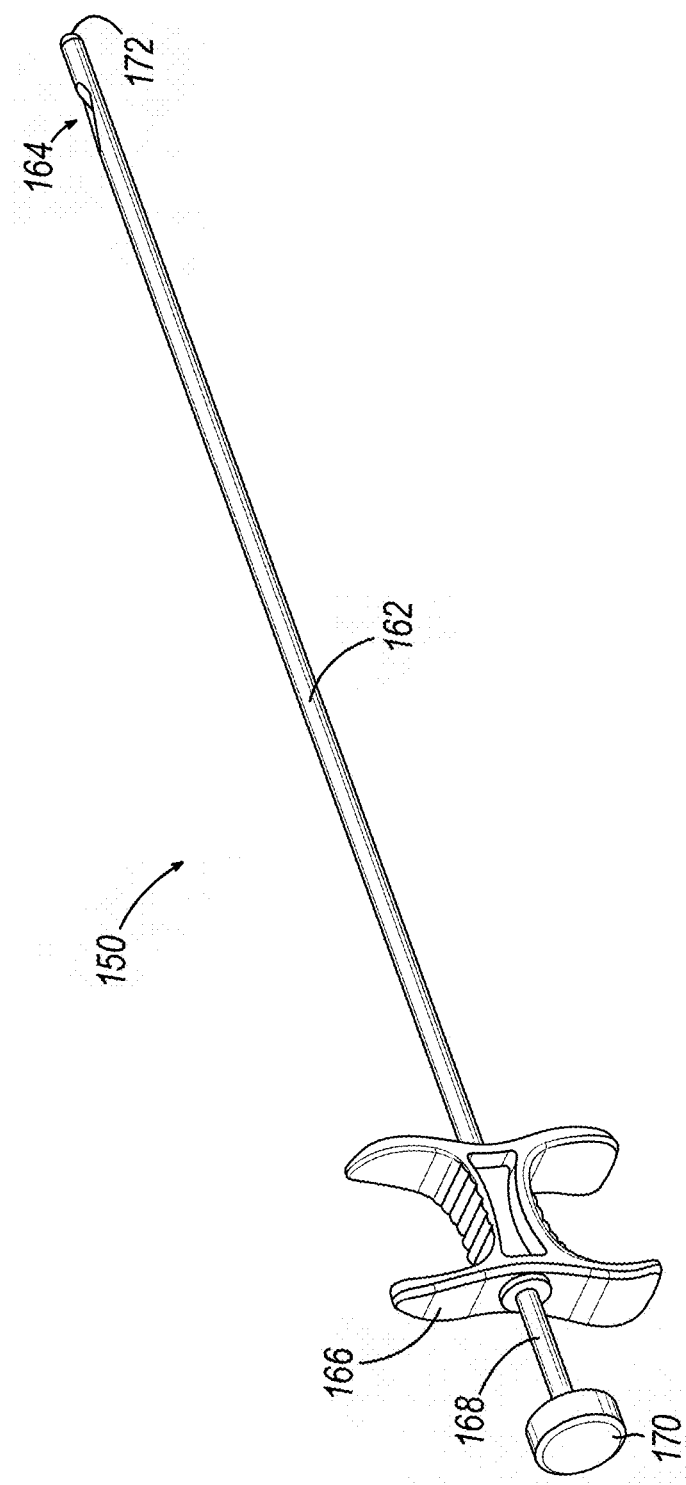
FIG. 2 depicts a perspective view of an exemplary marker delivery device.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

It will be appreciated that the terms "proximal" and "distal" are used herein with reference to an operator gripping housing. Thus, a tip of a cannula is distal with respect to the more proximal housing. It will be further appreciated that, for convenience and clarity, spatial terms such as "axial," and "longitudinal" also are used herein for reference to relative positions and directions. However, surgical instruments are used in many orientations and positions, and these terms are not intended to be limiting and absolute.

It may be beneficial to be able to mark the location or margins of a lesion, whether temporarily or permanently, prior to or immediately after removing or sampling it. Marking prior to removal may help to ensure that the entire lesion is excised, if desired. Alternatively, if the lesion were inadvertently removed in its entirety, marking the biopsy site immediately after the procedure would enable reestablishment of its location for future identification.

Once a marker is positioned at a biopsy site, it may be desirable for the marker to remain visible under ultrasound. It may also be desirable to make the marker readily identifiable relative to other structural features of a patient. For instance, it may be desirable for the marker to be distinguishable under ultrasound visualization from microcalcifications to avoid inadvertently characterizing the marker as a microcalcification during subsequent ultrasonic examinations. Generally, microcalcifications are used in the field to identify suspicious lesions or masses. Thus, it is generally desirable for the ultrasound view to be distinguishable as a marker and not inadvertently identified as a new mass.

I. Exemplary Marker

Aspects presented herein relate to devices and procedures for manufacturing a marker for percutaneously marking a biopsy cavity (10) having surrounding tissue (30), as shown in FIGS. 1A-1C. For instance, as seen in FIG. 1A, a marker (100) may be initially placed in the biopsy cavity (10) to facilitate relocation of the biopsy site. Marker (100) may comprise a carrier (120) and a marker element (12). Carrier (120) generally includes a bioabsorbable marker material (122). Thus, carrier (120) is generally configured for absorption into a patient after placement of marker (100) within the biopsy cavity (10). In some examples, carrier (120) can include a plurality of microbubbles to enhance visualization of carrier (120) under ultrasound. As will be described in greater detail below, marker material (122) is generally bioabsorbable such that marker material (122) may be generally absorbed into the patient's tissue over time. In the present example, marker material (122) comprises a hydrogel that is initially in a dehydrated state. Although a hydrogel is used in the present example, it should be understood that in other examples marker material (122) may comprise other known bioabsorbable materials In the present example, marker (100) further includes a marker element (12) that is generally not bioabsorbable. Marker element (12) may comprise a radiopaque or echogenic marker embedded within the bioabsorbable marker material (122) of carrier (120). For instance, marker element (12) may comprise metal, hard plastic, or other radiopaque or hyperechoic materials known to those of ordinary skill in the art in view of the teachings herein. In other examples, marker (100) may be formed without a marker element (12). In still other examples, marker (100) may be formed with only marker element (12) such that carrier (120) is omitted and marker element (12) is in a "bare" form. In other words, in some examples, marker (100) is formed of only carrier (120) as a bare clip.

Marker material (122) is generally expandable once disposed within a patient at a biopsy site. As shown in FIGS. 1B and 1C, the initially dehydrated marker material (122) may absorb fluid from the surrounding tissue (30) into which it is inserted. In response to this absorption of fluid, maker material (122) may swell, thereby permitting carrier (120) to fill a cavity formed at a biopsy site by removal of tissue samples during a biopsy procedure. Biodegradable materials may be particularly suitable in applications where it is desired that natural tissue growth be permitted to completely or partially replace the implanted material over time. Accordingly, biocompatibility is ensured, and the natural mechanical parameters of the tissue are substantially restored to those of the pre-damaged condition.

Marker (100) may be inserted into the body either surgically via an opening in the body cavity (30), or through a minimally invasive procedure using such devices as a catheter, introducer or similar type insertion device. Marker (100) may be delivered immediately after removal of the tissue specimen using the same device used to remove the tissue specimen itself. Follow-up noninvasive detection techniques, such as x-ray mammography or ultrasound may then be used by the physician to identify, locate, and monitor the biopsy cavity site over a period of time via marker (100).

Marker (100) of the present example is large enough to be readily visible to a clinician under x-ray or ultrasonic viewing, for example; yet small enough to be able to be percutaneously deployed into the biopsy cavity and to not cause any difficulties with the patient. Although examples are described in connection with treatment and diagnosis of breast tissue, aspects presented herein may be used for markers in any internal, tissue, e.g., in breast tissue, lung tissue, prostate tissue, lymph gland tissue, etc.

The hydration of the marker material (122) of carrier (120) by the natural moisture of the tissue surrounding it causes expansion of the polymer and thus minimizes the risk of migration. The growing hydrogel-based marker material (122) centers marker (100) in the biopsy cavity as it grows. As the hydrogel expands, naturally present moisture from the surrounding tissue, the hydration enables increasing sound through transmission, appears more and more hypoechoic and is easy to visualize on follow up ultrasound studies.

The hydrated hydrogel marker material (122) of carrier (120) may also be used to frame permanent marker (12). The hypoechoic nature of the hydrated marker material (122) enables ultrasound visibility of the permanent marker (12) within the hydrogel hydrated marker material (122) because the permanent marker (12) is outlined as a specular reflector within a hypoechoic hydrated marker having a water-like nonreflective substrate.

II. Exemplary Marker Delivery Device

In some examples it may be desirable to deploy marker (100) described above within the body cavity (30) using certain marker delivery devices. For instance, FIGS. 2 and 3 show an exemplary marker delivery device (150) which includes an elongate outer cannula (162) having a marker exit, such as side opening (164) formed adjacent to, but spaced proximally from, the distal end of the cannula (162).

A grip (166) can be provided at the proximal end of cannula (162). A push rod (168) can be provided, with push rod (168) extending coaxially in cannula (162) such that push rod (168) is configured to translate within cannula (162) to displace one or more markers through side opening (164) (see FIG. 3). Rod (168) may have sufficient rigidity in compression to push a marker from an internal lumen (165) of cannula (162) out through side opening (164) yet be relatively flexible in bending. A plunger (170) is coupled at the proximal end of push rod (168) for forcing push rod (168) distally in cannula (162) to deploy a marker out of cannula (162).

A user may grasp grip (166) with two fingers and push on plunger (170) using the thumb on the same hand, so that marker delivery device (160) is operated by a user's single hand. A spring (not shown) or another feature may be provided about push rod (168) to bias push rod (168) proximally relative to grip (166) and cannula (162).

Figure 3:
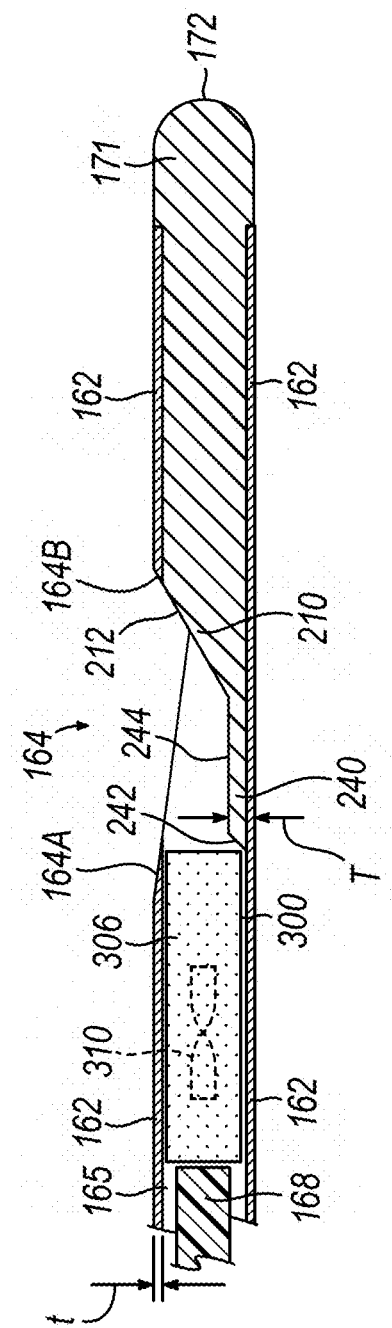
FIG. 3 depicts a side cross-sectional view of the marker delivery device of FIG. 2.

FIG. 3 shows a cross-sectional view of a distal portion of marker delivery device (150). As can be seen, a biopsy marker (300), similar to marker (100) described above, is disposed within internal lumen (165) of cannula (162). In the present example, marker (300) comprise a biodegradable or otherwise resorbable marker material (306), such as a generally cylindrically shaped body of collagen, hydrogel, or etc., and a metallic, generally radiopaque permanent marker or marker element (310) (shown in phantom) disposed within or otherwise carried by marker material (306).

Cannula (162) may be formed of any suitable metallic or non-metallic material. In some examples, cannula (162) is formed of a thin walled hollow tube formed of a suitable medical grade plastic or polymer. One suitable material is a thermoplastic elastomer, such as Polyether block amide (PEBA), such as is known under the tradename PEBAX®. Cannula (162) may be formed of PEBAX® and may be substantially transparent to visible light and X-ray.

Side opening (164) may be formed by cutting away a portion of the wall of cannula (162). Side opening (164) communicates with an internal lumen (165) of cannula (162). Side opening (164) may extend axially (in a direction parallel to the axis of lumen (165)) from a proximal opening end (164A) to a distal opening end (164B), as illustrated in FIG. 3.

In the present example, distal tip (172) extends from the distal end of cannula (162) and is rounded as shown in FIG. 3. Referring to FIG. 3, the distal end of cannula (162) is closed by a unitary endpiece (171), with a portion of endpiece (171) extending into internal lumen (165) of cannula (162). Endpiece (171) may be a molded or cast component. Endpiece (171) comprises a tip (172), a ramp (210) having a ramp surface (212), and a marker engaging element (240). Ramp surface (212) aids in directing marker (300) from internal lumen (165) through side opening (164). Marker engaging element (240) helps to retain marker (300) in internal lumen (165) until the user intends to deploy marker (300).

Marker engaging element (240) is disposed within internal lumen (165), and at least a portion of marker engaging element (240) is disposed distally of proximal end (164A) of side opening (164). Marker engaging element (240) extends along a portion of the floor of cannula (162) under opening (164) such that marker engaging element (240) is positioned to reinforce the portion of cannula (162) in which opening (164) is formed. For instance, by positioning marker engaging element (240) underneath opening (164), as shown in FIG. 3, element (240) helps to stiffen cannula (162) in the region where wall of cannula (162) is cut to form opening (164). As shown in FIG. 3, marker engaging element (240) extends from the proximal most portion of ramp surface (212) and does not extend proximally of side opening (164), though in other examples, a portion of element (240) may extend proximally of opening (164).

As shown in FIG. 3, marker engaging element (240) is in the form of a step having a generally uniform thickness (T) along element's (240) axial length, except that element (240) has a tapered proximal end (242). Tapered proximal end (242) forms an included angle with the longitudinal axis of lumen (165) (included angle with a horizontal line in FIG. 3) of about 45 degrees, while ramp surface (212) forms an included angle with the longitudinal axis of about 30 degrees. Of course, any number of other suitable angles may be used.

As shown in FIG. 3, an upwardly facing surface (244) (surface facing opening (164)) of marker engaging element (240) extends distally to contact ramp surface (212), so that there is not a space or gap between surface (244) and ramp surface (212). Such an arrangement is advantageous to reduce the possibility that marker (300), upon moving past marker engaging element (240), may become lodged between marker engagement element (240) and ramp (212). In some examples, marker engaging element (240), ramp (210), and/or tip (172) are formed of, or include, a material that is relatively more radiopaque than the wall of cannula (162). For instance, where element (240), ramp (210), and tip (172) are formed as an integral endpiece (171), endpiece (171) may include a radiopaque additive, such as barium sulfate. For instance, endpiece (171) may be a component molded of PEBAX®, with about 20 percent by weight barium sulfate added to the molten PEBAX® mold composition. The relatively more radiopaque marker engaging element (240), ramp (210), and tip (22) may be useful in distinguishing the position of those components using radiographic imaging. Also, where ramp (210) and/or step of engaging element (240) are positioned in association with opening (164), the addition of a radiopaque material can help identify the position of opening (164), and the position of marker (300) relative to opening (164) before, during, or after deployment of marker (300).

Figure 4:
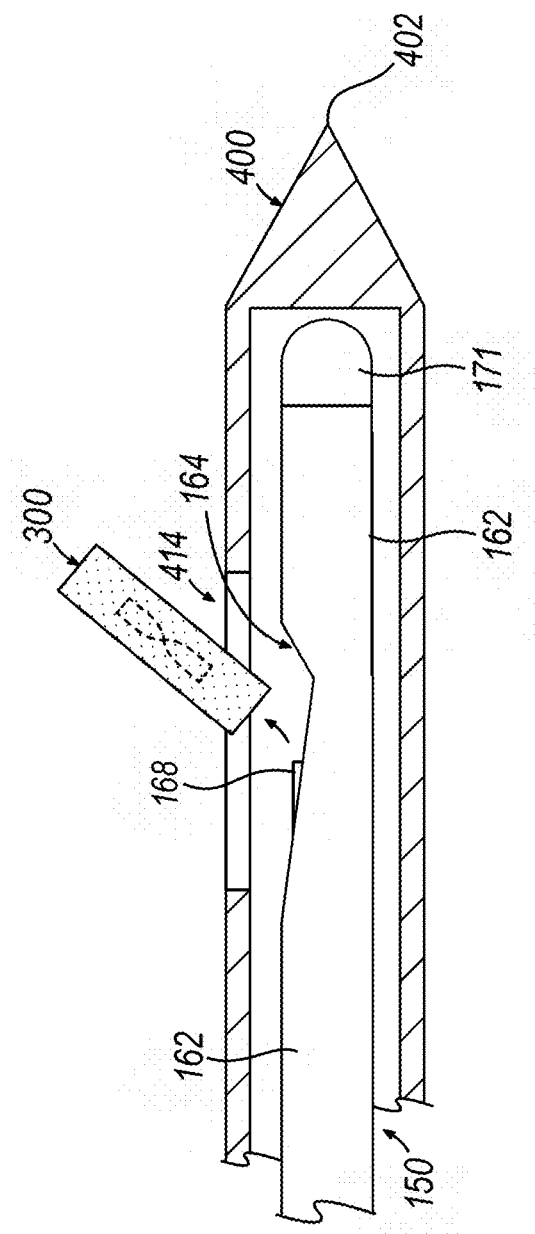
FIG. 4 depicts a cross-sectional view of a marker being deployed from the distal portion of the marker delivery device of FIG. 1 and through a lateral aperture in a biopsy needle to mark a biopsy site.

Referring to FIG. 4, marker delivery device (160) is used to deploy a marker (300) to mark a biopsy location within a patient. In FIG. 4, a biopsy needle (400) is shown having a closed distal end with piercing tip (402) and a lateral tissue receiving aperture (414). Marker delivery device (160) is introduced to a biopsy site through biopsy needle (400), which may be the same needle (400) used to collect a tissue sample from the biopsy site. Biopsy needle (400) may be of the type used with single insertion, multiple sample vacuum assisted biopsy devices. Several such biopsy devices are disclosed in the various patents and patent applications that have been referred to and incorporated by reference herein, though other biopsy devices may be used.

FIG. 4 shows the distal end of marker delivery device (160) disposed within needle (400). Needle (400) may be positioned in tissue, and a biopsy sample may be obtained through lateral aperture (414), thereby providing a biopsy cavity adjacent lateral aperture (414). Then, after the tissue sample has been obtained and transferred proximally through needle (400), and without removing needle (400) from the patient's tissue, marker delivery device (160) is inserted into a proximal opening in needle (400). In FIG. 4, needle (400) and marker delivery device (160) are positioned such that opening (164) of cannula (162) and lateral aperture (414) of needle (400) are substantially aligned axially and circumferentially. Then, with marker delivery device (160) and needle (400) so positioned at the biopsy site, push rod (168) is advanced to deploy marker (300) up ramp surface (212), through opening (164), and then through lateral aperture (414), into the biopsy cavity.

Figure 5:
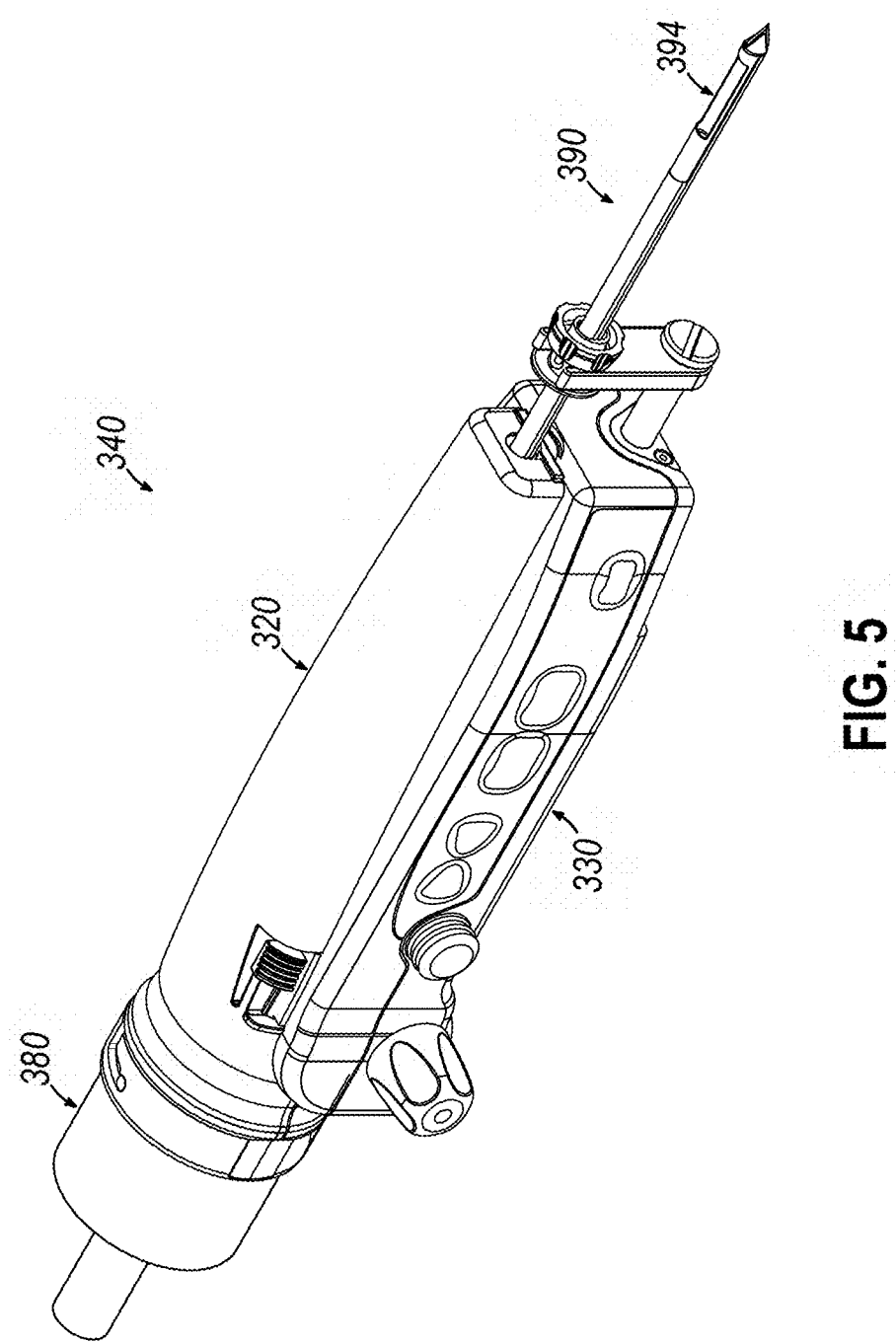
FIG. 5 depicts a perspective view of an exemplary biopsy device.

FIG. 5 shows a biopsy device (340) including a holster (320), a probe (330), and a tissue sample holder (380). Holster (320) of the present example includes various internal components configured to drive various functions of biopsy device (340). For instance, in some examples, holster (320) may include a motor (not shown), a rotating member (not shown), and one or more holster gears (not shown). In such examples, the motor may be in communication with the rotating member to drive movement of various components via the rotating member such as one or more holster gears. Holster (320) is operatively connected to probe (330) and tissue sample holder (380) is operatively connected to the proximal end of probe (330).

Figure 6:
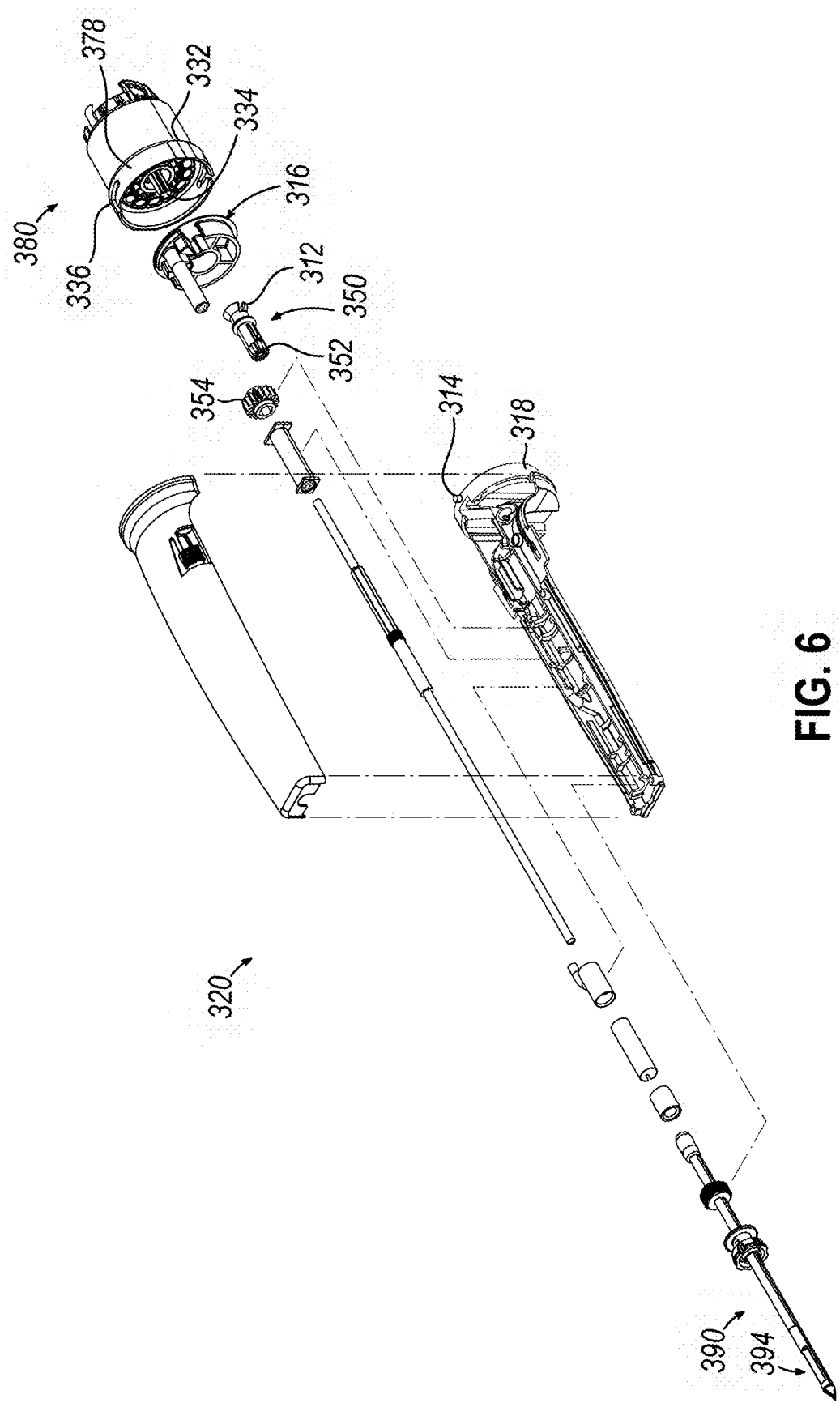
FIG. 6 depicts an exploded perspective view of a probe and manifold of the biopsy device of FIG. 5.

FIG. 6 shows probe (330) of biopsy device (340) in greater detail. Probe (320) includes a needle (400), a lateral aperture (414), a manifold ring (318), a proximal face (316), and a pair of pins (314). In some examples, probe (320) also includes an accessory gear (352), an accessory shaft (350) (also may be referred to as a shaft adaptor), a gripping member (312), and a manifold shaft (334). Accessory gear (352) is operatively connected to the distal end of accessory shaft (350) and the gripping member (312) is operatively connected to the proximal end of accessory shaft (350). Accessory gear (352) is in communication with the one or more holster gears of holster (320), as described above.

Tissue sample holder (380) of the present example is generally configured to collect one or more tissue samples therein. Although not shown, it should be understood that in some examples, tissue sample holder (380) can include a rotatable member having a plurality of chambers. Such a rotatable member may be configured to receive a tissue sample tray within each chamber of the plurality of chambers. The rotatable member may then be rotated sequentially to collect one or more tissue samples within each tissue sample tray. In some examples, tissue sample holder (380) can be configured in accordance with at least some of the teachings of US Pub. No. 2018/0221002, entitled "Biopsy System," published Aug. 9, 2018, the disclosure of which is incorporated by reference herein.

Tissue sample holder (380) includes a coupler (378) configured to couple at least a portion of tissue sample holder (380) to probe (320). Coupler (378) includes an annular ring (332) and a latching feature (336). As will be described in greater detail below, in some examples, latching feature (336) may be configured to receive one or more components of probe (320) to couple tissue sample holder (380) to probe (320) similar to a bayonet fitting or other mechanical fastener.

In order to couple tissue sample holder (380) to probe (320), a pair of latching features (336) are aligned with a pair of pins (314) on manifold ring (318). Annular ring (332) is moved longitudinally over manifold ring (318). Tissue sample holder (380) is then rotated to a locked position. In the locked position, latching features (336) engages pair of pins (314) and retains tissue sample holder (380).

As noted above, in some examples, one or more portions of tissue sample holder (380) can be configured to rotate to facilitate collection of one or more tissue samples within a plurality of chambers of tissue sample holder (380). To facilitate such functionality, tissue sample holder (380) includes manifold shaft (334), which is configured to engage one or more components of probe (320) to thereby communicate rotary motion from probe (320) to tissue sample holder (380).

As noted above, probe (330) includes a gripping member (312) associated with an accessory shaft (350). Gripping member (313) is configured to receive a distal end of manifold shaft (334) of tissue sample holder (380). Griping member (313) is in communication with accessory shaft (350) such that rotation of accessory shaft (350) may be communicated to manifold shaft (334) to thereby rotate at least a portion of tissue sample holder (380) via gripping member (312).

III. Exemplary Coiled Rack Marker Delivery Device

In some examples, it may be desirable to side-deploy a marker from a lateral aperture of a needle. In particular, in some examples, it may be desirable to deploy a marker through a marker delivery device similar to marker delivery device (150) (see FIG. 2) described above but utilizing a push rod directly inserted into a needle similar to needle (390, 400). In particular, as described above some marker delivery devices can be equipped with an elongate cannula that can be configured for insertion into needle (390, 400). This configuration can present challenges with manipulation of the marker delivery device due to the flexibility of the cannula and the diameter relative to the axial length. Thus, in some examples it may be desirable to omit the cannula entirely and insert a push rod directly into needle (390, 400). While various examples of suitable devices for providing marker deployment through the distal end of a marker delivery device are described herein, various alternative configurations may be used as will be apparent to those of ordinary skill in the art in view of the teachings herein.

A. Exemplary Coiled Rack Marker Device with Attached Cannula

Figure 7:
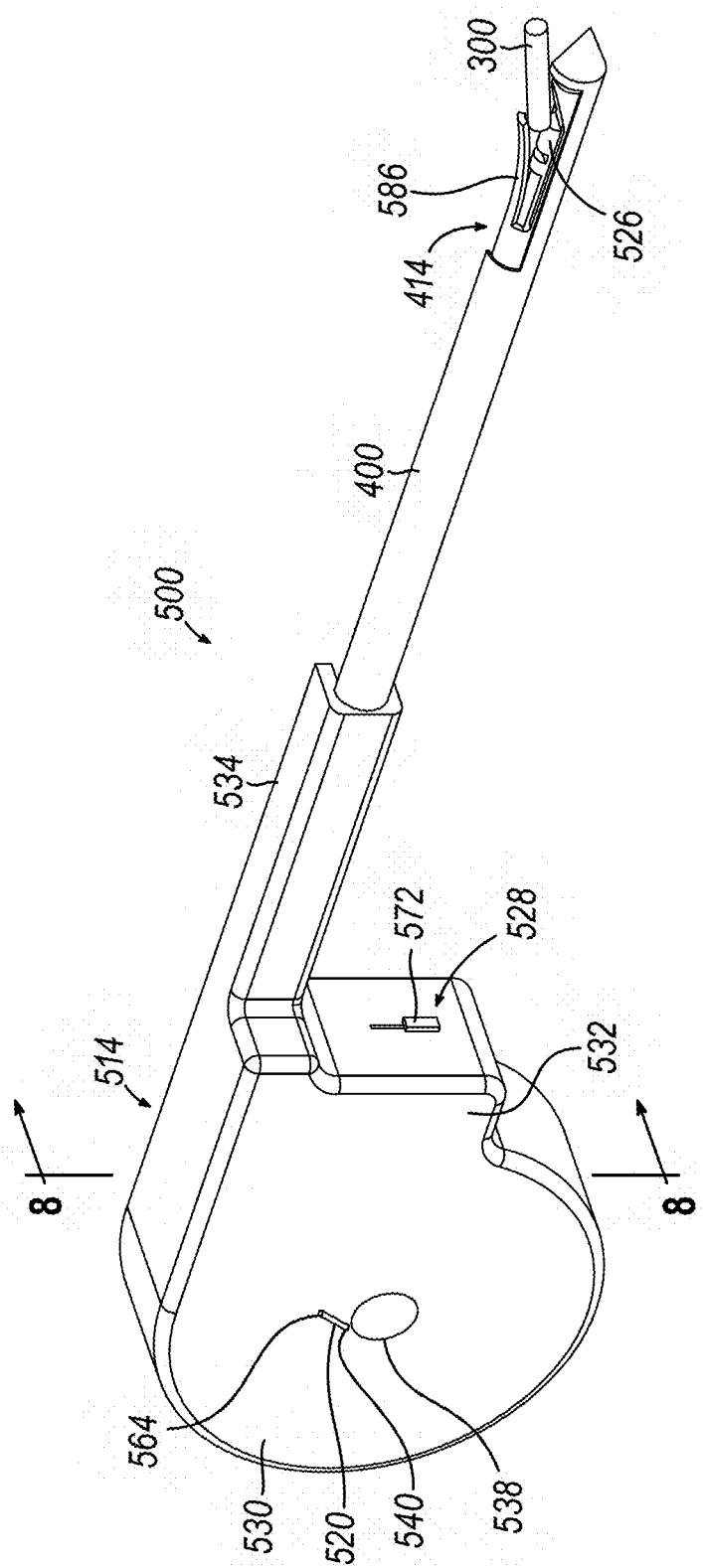
FIG. 7 depicts a perspective view of another exemplary marker delivery device.
Figure 8:
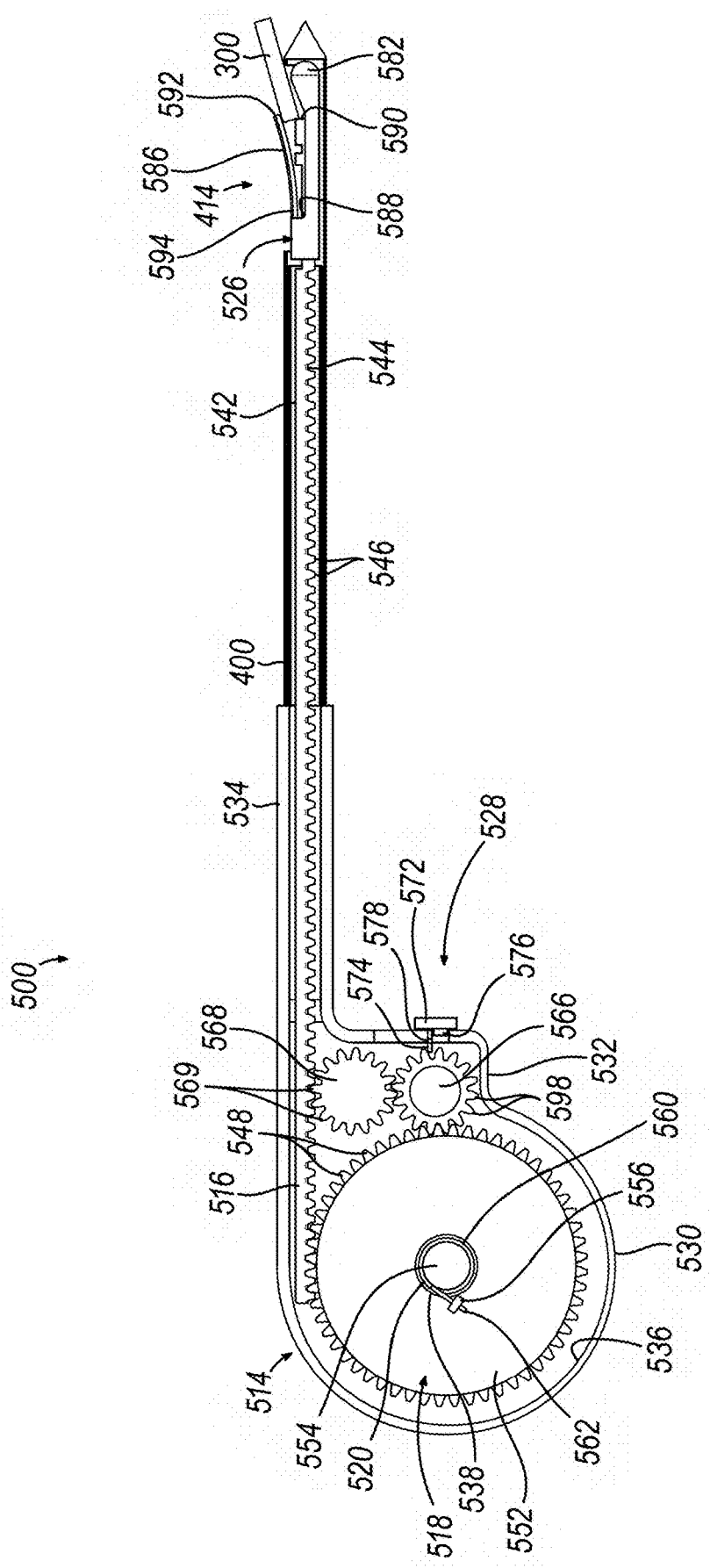
FIG. 8 depicts a side cross-sectional view of the marker delivery device of FIG. 7, taken along line 8-8 of FIG. 7.

FIGS. 7-8 show an exemplary marker delivery device (500) that is generally configured to deploy marker (300) through a lateral aperture of a biopsy needle. It should be understood that marker delivery device (500) substantially similar to marker delivery device (150) (see FIG. 2) unless otherwise described herein. Like marker delivery device (150) described above, at least a portion of marker delivery device (500) is insertable into needle (400) or needle (390) to deploy marker (300) through lateral aperture (414). Additionally, marker deliver device (150) includes a housing (514) configured to be gripped by the operator similar to grip (166) described above.

Unlike marker delivery device (150) described above, marker delivery device (500) of the present example is configured for insertion into needle (400) or needle (390) without the use of structures similar to outer cannula (162). Also, unlike marker delivery device (150) described above, marker delivery device (500) of the present example is generally configured to drive various components thereof using a coordinated linear and rotational motion to deploy marker (300).

FIG. 7 shows housing (514) of marker delivery device (500) in detail. As can be seen, housing (514) includes an annular portion (530), a rectangular portion (532), and an elongate portion (534). Rectangular portion (532) extends distally from annular portion (530) to elongate portion (534). Rectangular portion (532) is substantially rectangular in shape and is generally configured to be gripped by an operator. Rectangular portion (532) can be any suitable shape. For instance, in some examples, rectangular portion (532) may be arcuate, or triangular. In addition or in the alternative, rectangular portion (532) may extend from annular portion (530) to form a pistol grip Elongate portion (534) extends distally from rectangular portion (532). In some examples, a distal end of elongate portion (534) may be configured to abut a proximal end of needle (400) as shown in FIG. 7. Additionally, elongate portion (534) may be further configured for insertion into one or more components of a biopsy device. For instance, and as will be described in greater detail below, elongate portion (534) may be configured for insertion into tissue sample holder (380) for deployment of marker (300) through needle (390). Regardless, elongate portion (534) is generally tubular in shape. Although elongate portion (534), is shown as having a generally square tubular shape, it should be understood that a variety of other suitable shapes may be used such as an elongate cross-section that is rectangular, triangular, or oval-like in shape.

Although not shown, it should be understood that in some examples, housing (514) may include a coupler or other structures configured to couple marker delivery device (500) to structures associated with needle (400) such as a housing of a probe similar to probe (330) described above. In some examples, such couplers may include an annular ring, latching features, or other similar features configured to engage one or more corresponding structures associated with needle (400). Suitable couplers that may be readily incorporated into housing (514) are described in greater detail below in connection with marker delivery device (600).

As best seen in FIG. 8, the interior of housing (514) includes a flexible push rod (516), a rack stowage drum (518), a spring (520), an idler gear (566), a rack drive gear (568), a deployer tip (526), and a release mechanism (528). As can be seen, annular portion (530) defines an interior surface (536), a drum aperture (538), and a spring retainer aperture (540). Interior surface (536), drum aperture (538), and spring retainer aperture (540) are together configured to contain and/or hold at least a portion of flexible push rod (516), rack stowage drum (518), spring (520), idler gear (566), rack drive gear (568), deployer tip (526), and release mechanism (528), as will be described in greater detail below.

Flexible push rod (516) is generally configured to be compressively rigid for deployment of marker (300), yet flexible for manipulation within housing (514). Thus, flexible push rod (516) may a variety of suitable materials having rigid, yet flexible properties. For example, flexible push rod (516) may comprise polymers, natural or synthetic rubbers, silicone, and/or etc.

Flexible push rod (516) includes a smooth side (542) and a rack teeth side (544). Smooth side (542) is configured to slidably engage the interior of housing (514) and/or needle (400). Thus, it should be understood that smooth side (542) is generally configured to reduce friction between interior surfaces of housing (514) and/or needle (400) and flexible push rod (516). To further reduce friction, in some examples, flexible push rod (516) may be additionally lubricated with a sterile grease or oil. In addition, or in the alternative, flexible push rod (516) may be lubricated with saline or any other suitable medical fluid known in the art to have lubricating properties.

Rack teeth side (544) includes a transverse drive surface in the form of a set of rack teeth (546). As will be described in greater detail below, rack teeth (546) are generally configured to mate with at least a portion of rack stowage drum (518) to drive movement of flexible push rod (516). Although rack teeth (546) in the present example are shown and described as teeth, it should be understood that other suitable transverse drive surfaces may be used. For instance, in some examples, rack teeth (546) may alternatively be configured as cogs, or arcuate beads, and/or etc. As such, in some examples, flexible push rod (516) may be referred to as a flexible rack, a flexible beaded rod, a flexible deployment rod, and/or etc.

Rack stowage drum (518) is positioned within the interior of housing (514) as is generally configured to both store and drive movement of flexible (516) push rod. In some examples, rack stowage drum (518) may alternatively be referred to as a wheel, a drum, a push rod driver, a gear, and/or etc. Rack stowage drum (518) has a drum portion (552), a drum shaft (554), a drum spring retainer (556), and drum gear teeth (548). In some examples, stowage drum (518) may be formed as a single integral piece of molded plastic, brass, or aluminum. Drum portion (552) may also be press fit or glued on a separate drum shaft (554).

Drum shaft (554) is rotationally coupled to housing (514) through drum aperture (538). In particular, drum shaft (554) extends through housing (514) via drum aperture (538) to rotatably secure rack stowage drum (518) within housing (514) via drum shaft (554). Alternatively, housing (514) can have another retaining feature (not shown) that rotatably couples drum shaft (554) to interior surface of housing (536). In some examples, stowage drum (518) may additionally be fitted with a pair of bearings (not shown) fixed to drum shaft (554). Such bearings can be fixedly coupled to housing (514) and rotatably coupled to drum shaft (554).

Drum spring retainer (556) is positioned proximate drum shaft (554) on drum portion (552). Drum spring retainer (556) is generally configured to receive or otherwise engage at least a portion of spring (520). As will be described in greater detail below, such engagement between drum spring retainer (556) and spring (520) is generally configured to drive rotation of rack stowage drum (518) via spring (520).

As noted above, rack stowage drum (518) includes a transverse drive surface in the form of a plurality of drum gear teeth (548) oriented around a circular outer surface of rack stowage drum (518). As described above, drum gear teeth (548) are generally configured to engage rack teeth (546) of flexible push rod (516). As will be described in greater detail below, such engagement may be used to convert rotary motion of rack stowage drum (518) into movement of flexible push rod (516).

Spring (520) is positioned within housing (514) proximate rack stowage drum (518) such that spring is generally configured to drive rotation of rack stowage drum (518). Spring (520) may thus comprise a variety of resilient materials such as metal, plastic, and/or etc. Spring (520) is configured to move between a biased state and a relaxed state. Spring has a helical portion (560), first spring end (562), and a second spring end (564). Helical portion (560) is wound around drum shaft (554). In some examples, drum shaft (554) may be hollow and helical portion (560) may be inside drum shaft (554). First spring end (562) is retained by drum spring retainer (556) and second spring end (564) is retained by spring retainer aperture (540) (see FIG. 7). As will be described in greater detail below, spring (520) is configured to be in the biased state when flexible push rod (516) is in a wound state and in the relaxed state when in flexible push rod (516) is in an unwound state.

Rectangular portion (532) of housing (514) houses idler gear (566), a rack drive gear (568), and a release mechanism (528). Idler gear (566) may be rotatably coupled within housing (514) similar to stowage drum (518) described above. Idler gear (566) of the present example generally comprises similar materials as stowage drum (518). Alternatively, in other examples, idler gear (566) can comprise different materials as will be apparent to those of ordinary skill in the art in view of the teachings herein. Although not shown, it should be understood that in other examples, idler gear (566) may additionally include bearings or other friction reducing features as similarly described above with respect to rack stowage drum (518) and drum shaft (554). Idler gear (566) is axially and transversely displaced in housing (514) in relation to stowage drum (518).

Idler gear (566) includes a plurality of idler teeth (598) oriented around an outer circular perimeter thereof. Each idler tooth (598) of idler teeth (598) is configured to mesh with a corresponding drum tooth (548) of drum teeth (548). Thus, idler gear (566) is positioned within housing (514) proximate rack stowage drum (518). As will be described in greater detail below, idler gear (566) is generally configured to engage various components of release mechanism (528) to selectively lock and unlock rotation of rack stowage drum (518). Although the term idler gear (566) is used herein, it should be understood that in other examples idler gear (566) may be referred to as a wheel, a gear, a lock mechanism, and/or etc.

As with idler gear (566) discussed above, rack drive gear (568) includes a plurality of teeth (569) oriented around an outer circular perimeter thereof. Rack drive gear (568) is also disposed within housing (514) proximate idler gear (566) such that teeth (569) are configured to engage idler teeth (598). Rack drive gear (568) is additionally positioned proximate flexible push rod (516) such that teeth (569) of rack drive gear (568) are configured to engage and support at least a portion of flexible push rod (516) via rack teeth (546). Thus, it should be understood that rack drive gear (568) is configured to keep flexible push rod (516) from being displaced downwardly in relation to a top of rectangular portion (532). Although the term rack gear (568) is used herein, it should be understood that in other examples rack gear (568) may also be referred to as a wheel, a gear, a support, and/or etc.

In some examples, marker delivery device (500) may only have a rack stowage drum (518) without an idler gear (566) and a rack drive gear (568). In such examples, rectangular portion (532) of housing (514) and can also be omitted. In absence of structures similar to rack drive gear (568), flexible push rod (516) can alternatively be supported by elongate portion (534) and/or other structures of housing (514).

Release mechanism (528) includes a button (572), a dog (574), a pivot point (578), and an arm (576). Although not shown, it should be understood that release mechanism (528) may additionally include a coil spring or other resilient feature to bias release mechanism (528). Button (572) is positioned in distal portion of housing (514) and is configured to be translated in the longitudinal direction. Arm (576) is rotatably coupled to pivot point (578). Arm (576) is coupled to dog (574). Dog (574) is removably coupled to idler gear (566).

Button (572) is configured to be actuated by an operator to begin the deployment sequence. In particular, button (572) engages arm (576). Arm (576) is configured to move about pivot point (578) when button (572) engages arm (576). Dog (574) is configured to hold idler gear (566) stationary with spring (520) under tension in the biased state and rack storage drum (518) in the wound state. In other examples, dog (574) may be removably coupled to rack drive gear (568) or stowage drum (518). Any other release mechanism (528) known in the art may be utilized that may removably couple to a gear.

Release mechanism (528) of the present example is positioned on a distal portion of housing (514). Although other positions can be used, the particular position shown may be desirable to permit portions of structures similar to probe (330) to actuate release mechanism (528). For instance, and as will be described in greater detail below, with release mechanism (528) in the position shown, release mechanism (528) may be automatically actuated by a portion of probe (330) or other similar components upon complete insertion of marker delivery device (500) into probe (330) via contact between button (572) and probe (330).

Figure 9:
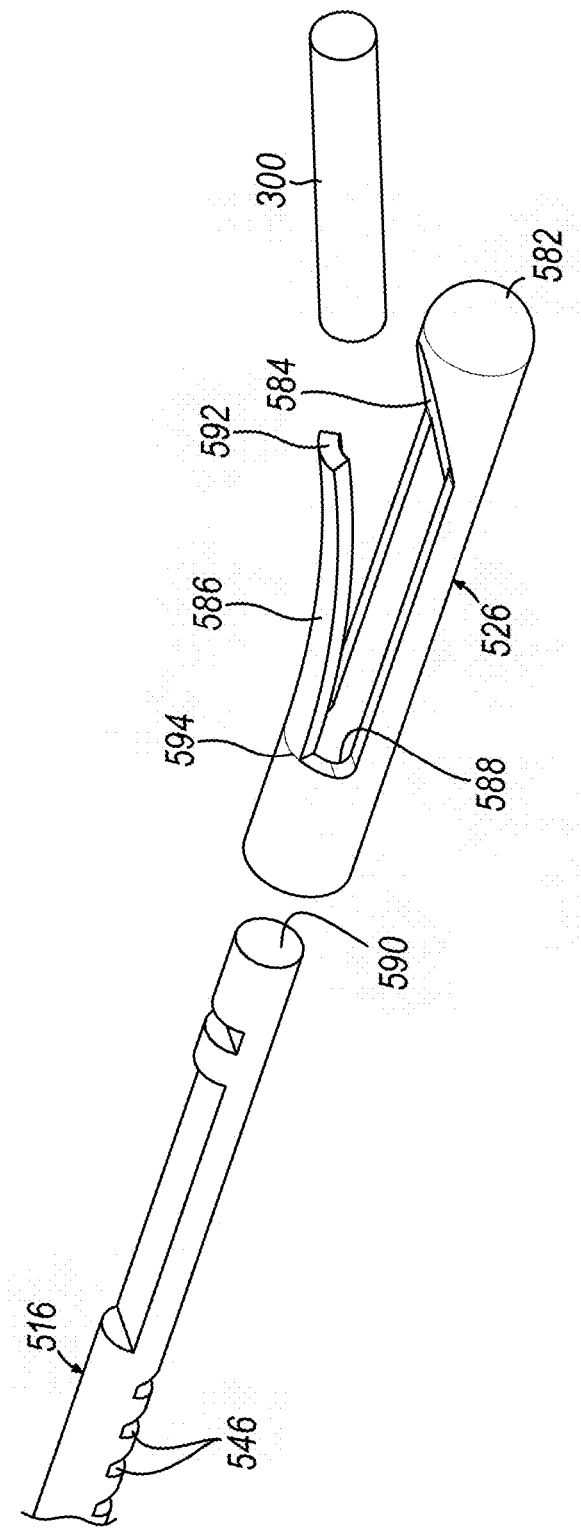
FIG. 9 depicts an exploded perspective view of a deployer tip of the marker delivery device of FIG. 7.

FIG. 9 shows deployer tip (526) in greater detail. As can be seen, deployer tip (526) includes a distal tip (582), a ramp (584), a flap (586), and a recess (588). Flexible push rod (516) is slidably disposed within a proximal end of deployer tip (526) in recess (588). Marker (300) is distally located in relation to flexible push rod (516) between ramp (584) and distal tip (590) of flexible push rod (516). Flap (586) is constructed from a material that has resilient properties. Flap (586) has a free end (592) and a hinged end (594). Flap (586) is biased to rotate about hinged end (594) in an arcuate path. Free end (592) is biased downwards by inner surface of biopsy needle (400) (see FIG. 8) to retain marker (300) within deployer tip (526).

FIGS. 10 through 13 show an exemplary use of marker delivery device (500) to deploy marker (300) through needle (400). Although marker delivery device (500) is described herein in the context of use with needle (400) and marker (300), it should be understood that in other uses, marker device device (500) may be readily used with other needles such as needle (390) and other markers without substantially departing from the use described herein.

Figure 10:
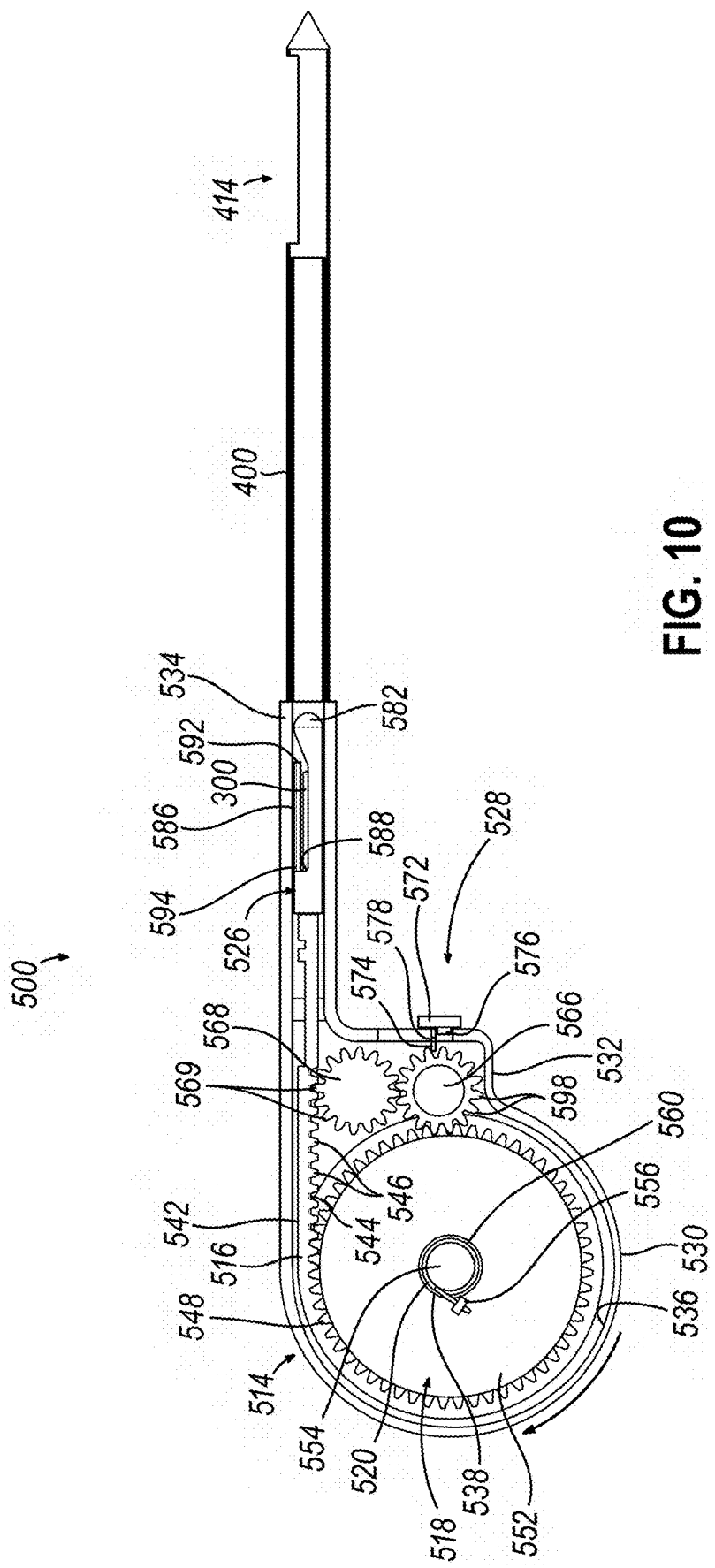
FIG. 10 depicts a side cross-sectional view of the marker delivery device of FIG. 7, with a cable in a wound state.
Figure 11:
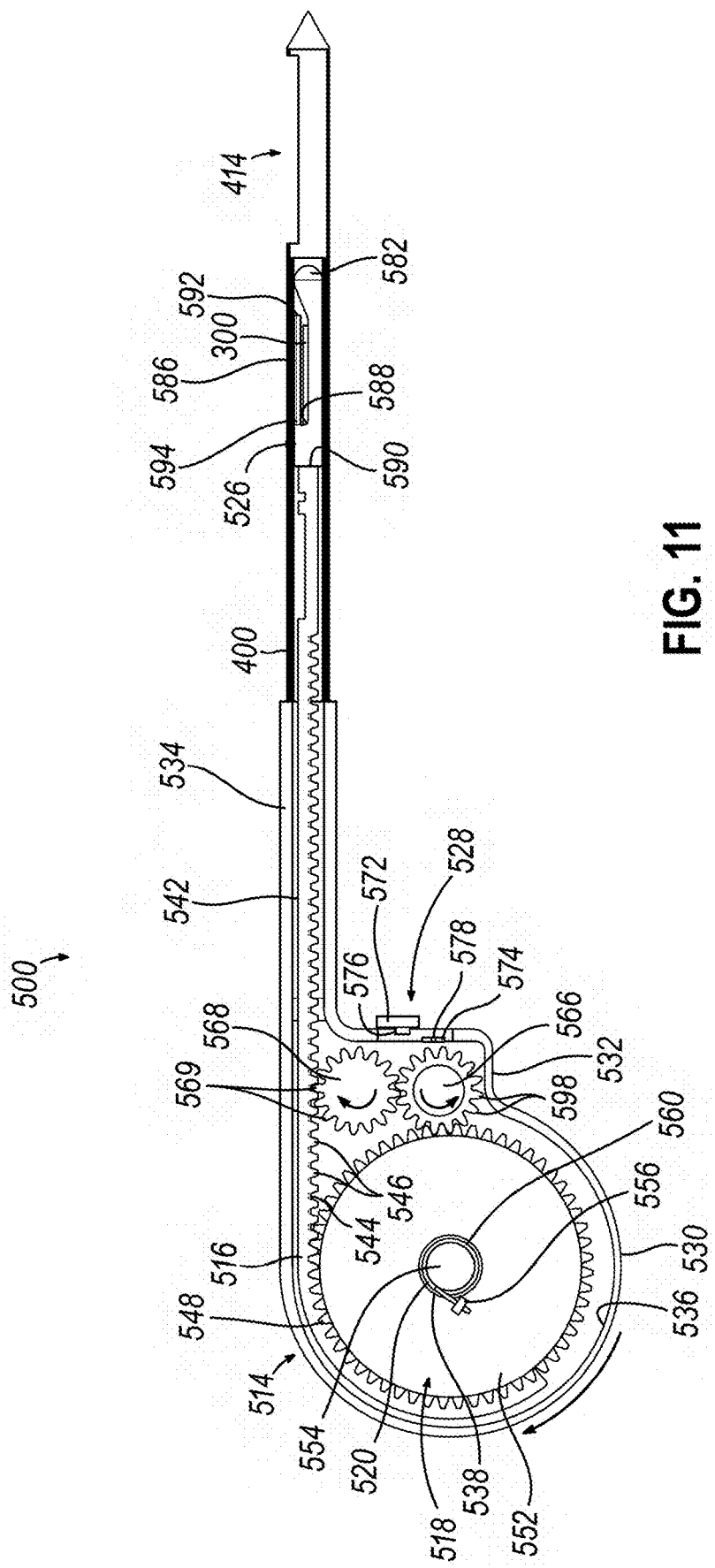
FIG. 11 depicts a side cross-sectional view of the marker delivery device of FIG. 7, with the cable in a partially unwound state.

In use, marker delivery device (500) is initially inserted into needle (400). As can be seen in FIG. 10, marker delivery device (500) is initially in the wound state when inserted into needle (400). In the wound state, flexible push rod (516) is retracted into a proximal position such that elongate portion (534) houses a portion of flexible push rod (516), marker (300) and deployer tip (526). Spring (520) is biased in the wound state. Flexible push rod (516) is substantially wound around rack stowage drum (518) with a portion of flexible push rod (516) extending distally from rack stowage drum (518) through a top of rectangular portion (532) and further extending through elongate portion (534).

Marker deliver device (500) is held in the wound state by release mechanism (528). In particular, release mechanism (528) engages idler gear (566) with dog (574) and thereby prevents idler gear (566) from rotating. Idler gear (566) engages rack drive gear (568). Idler gear (566) being in a state of rest keeps rack drive gear (568) in a state of rest. Rack drive gear (568) engages flexible push rod (516) and keeps flexible push rod (516) in a state or rest. Rack drive gear (568) keeps flexible push rod (516) from being rotationally driven. Flexible push rod (516) in a state of rest keeps rack stowage drum (518) from being rotated by spring (520). Spring (520) is biased to rotate stowage drum (518) in the clockwise direction.

To initiate deployment of marker (300), button (572) of release mechanism (528) can be actuated. Actuation of button (572) causes transition of marker delivery device (500) into a partially unwound state shown in FIG. 11. As can be seen, actuation of button (572) (either automatically by structures associated with needle (400) or manually by an operator) linearly translates button (572) proximally. This movement of button (572) pivots arm (576) to release dog (574) from idler gear (566). Idler gear (566) is then free to rotate, and no longer holds rack drive gear (568) stationary. Rack drive gear (568) no longer holds flexible push rod (516) stationary. Likewise, idler gear (566) no longer holds rack stowage drum (518) stationary.

Flexible push rod (516) begins to transition from a wound state to an unwound state. In particular, spring (520) rotates rack stowage drum (518) in a clockwise direction. Drum gear teeth (548) engage rack teeth (546) and begin to unwind flexible push rod (516) from stowage drum (518).

As flexible push rod (516) unwinds, a portion of flexible push rod (516) translates through needle (400) towards lateral aperture (414). Distal tip (590) of flexible push rod (516) exhibits longitudinal force on marker (300) and translates marker (300) distally. Inner surface of biopsy needle (400) biases flap (586) downwards so marker does not deploy. Marker (300) engages ramp (584) and translates deployer tip (526) distally in relation to the biopsy needle (400).

Figure 12:
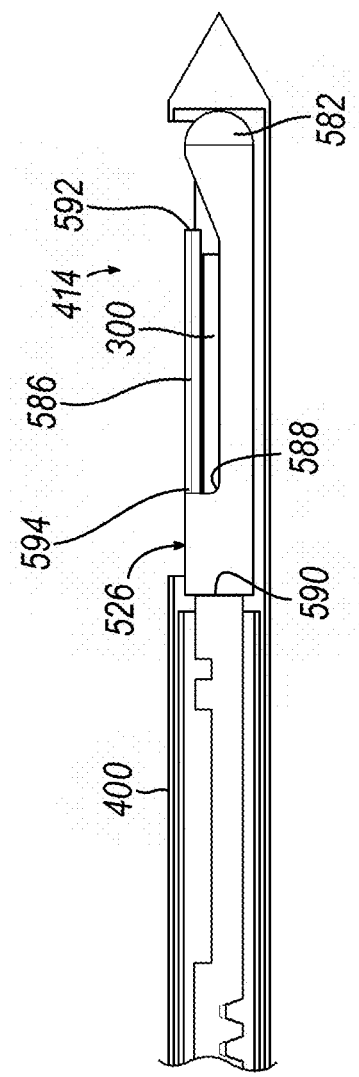
FIG. 12 depicts a side cross-sectional enlarged view of a distal portion of the marker delivery device of FIG. 7, with the cable in a partially unwound state and a marker in the undeployed state.

FIG. 12 shows a distal portion of biopsy needle (400) with deployer tip (526) fully deployed. In this position, deployer tip (526) has translated through biopsy needle (400). Also in this position, distal tip (582) of deployer tip (526) engages a proximal face the interior of needle (400). It should be understood that up to the position shown in FIG. 12, flexible push rod (516) and deployer tip (526) translate together in the same direction within needle (400). However, once distal tip (582) of deployer tip (526) contacts a proximal face needle (400), further translation of deployer tip (526) is prevented such that flexible push rod (516) may continue to translate within deployer tip (526), and relative to deployer tip (526). To facilitate such translation, spring (520) may continue to rotate rack stowage drum (518) in a clockwise direction while drum gear teeth (548) engage rack teeth (546), and flexible push rod (516) translates distally.

Figure 13:
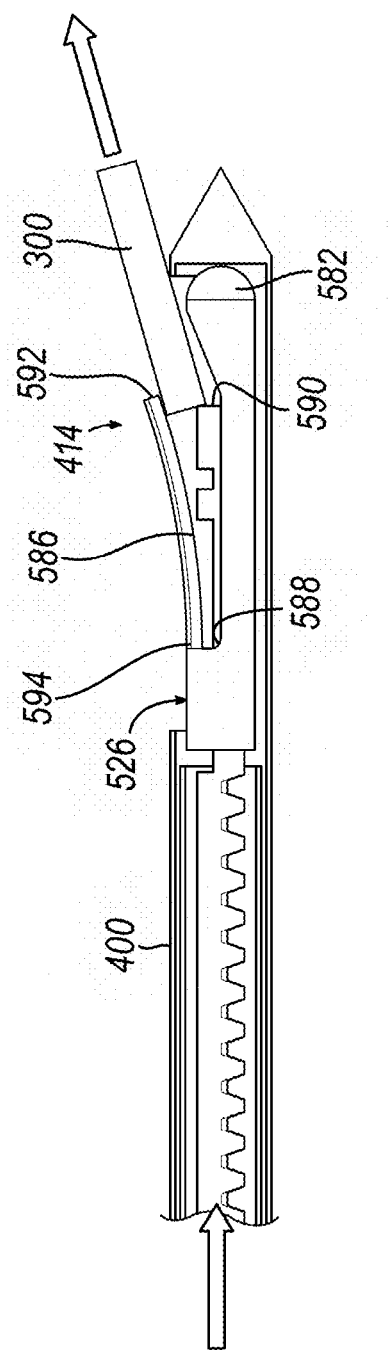
FIG. 13 depicts a side cross-sectional enlarged view of the distal portion of marker delivery device of FIG. 7, with the cable in an unwound state and the marker in the deployed state.

FIG. 13 shows a distal portion of biopsy needle (400) with marker (300) being deployed from deployer tip (526). In this position, the proximal face of needle (400) stops the linear translation of deployer tip (526). Flexible push rod (516) continues to be translated distally by spring (520). Distal tip (590) of flexible push rod (516) engages marker (300) and distally translates marker (300) relative to stationary deployer tip (526). Inner surface of biopsy needle (400) no longer biases flap (586) to keep flap (586) longitudinally aligned with inner surface of biopsy needle (400). Free end (592) moves in an arcuate path about hinged end (594) opening flap (586). Distal tip of push rod (590) pushes marker (300) up ramp (584) deploying marker (300) into tissue.

B. Exemplary Coiled Rack Marker Delivery Device with Biopsy Device Coupler

Figure 14:
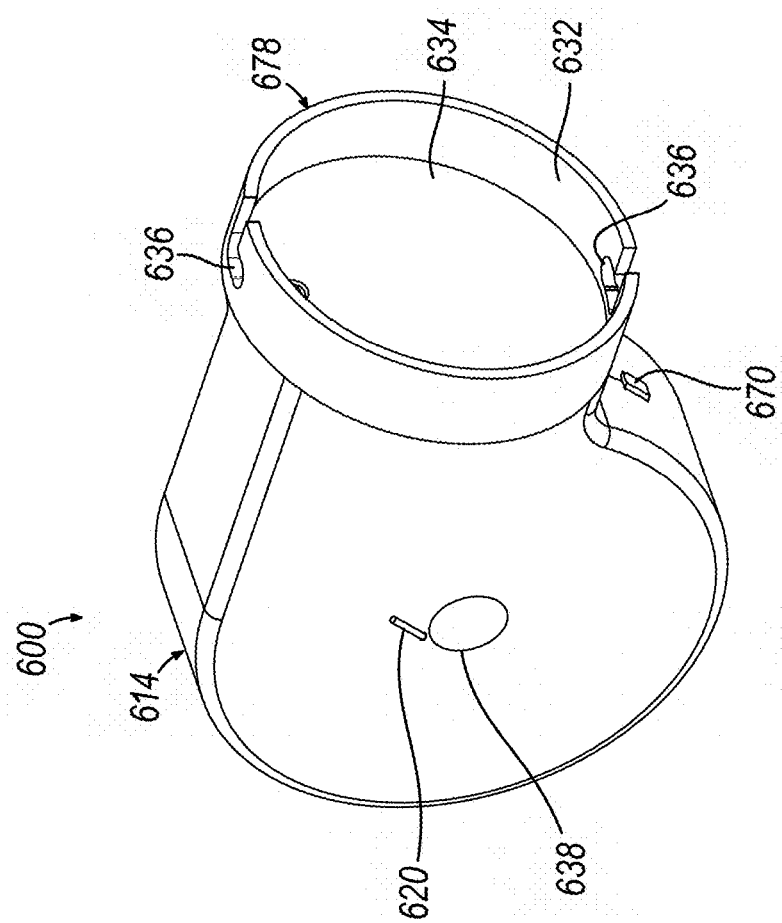
FIG. 14 depicts a perspective view of still another exemplary marker delivery device.
Figure 15:
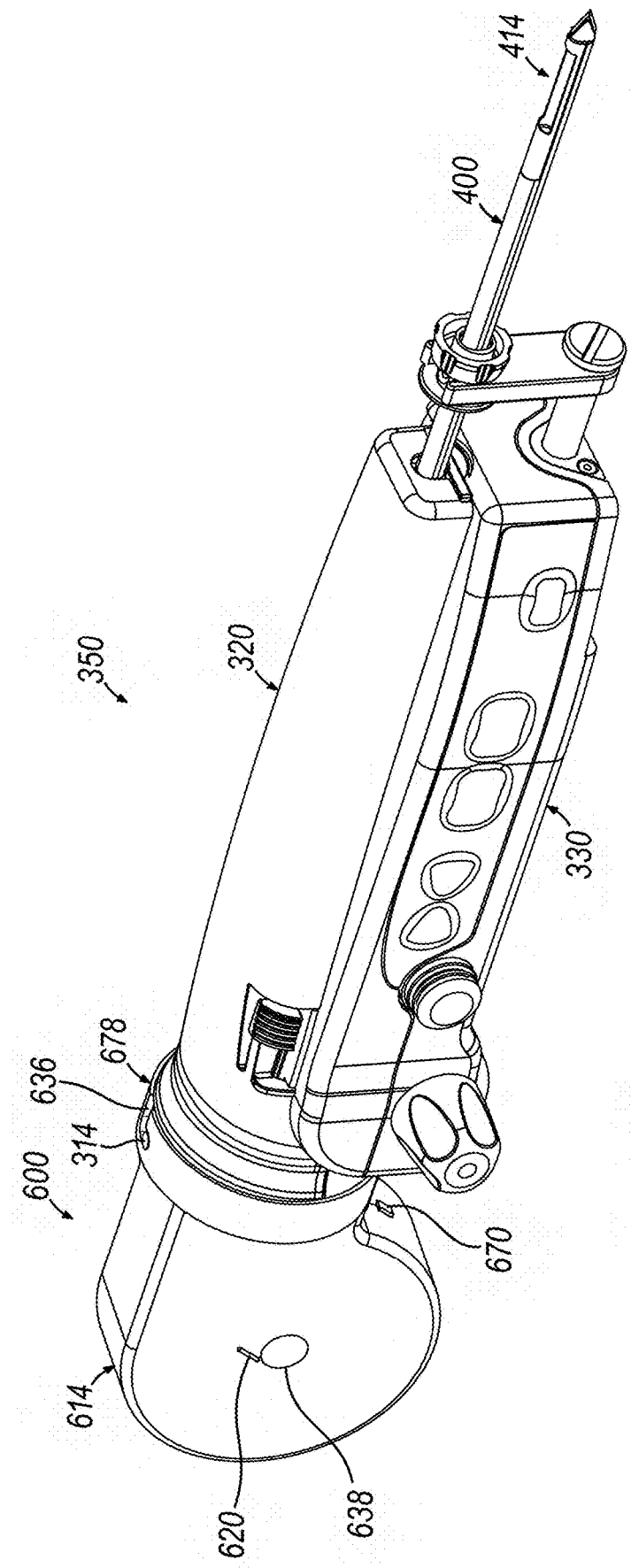
FIG. 15 depicts a perspective view of the marker delivery device of FIG. 14 coupled to the biopsy device of FIG. 5.

FIG. 14-15 shows another exemplary coiled rack marker delivery device (600) configured to couple to biopsy device (340) described above. FIG. 14 shows marker delivery device (600) in isolation; while FIG. 15 shows the marker delivery device (600) coupled to the proximal end of biopsy device (340). Marker delivery device (600) is substantially similar to marker delivery device (500) discussed above. For instance, although not shown, it should be understood that marker delivery device (600) likewise includes structures substantially similar to flexible push rod (516), deployer tip (526), spring (520), rack stowage drum (518), idler gear (566), a rack drive gear (568), and release mechanism (528) described above.

As with marker delivery device (500) described above, marker delivery device (600) of the present example includes a spring (620) and a release mechanism (670). Such features of marker delivery device (600) operate similarly to corresponding features of marker delivery device (500) described above. For instance, as with spring (520), spring (620) of the present example is disposed within marker delivery device (600) to drive rotation of a mechanism similar to rack stowage drum (518), which in-turn drives a feature similar to flexible push rod (516) distally for deployment of marker (300). Similarly, as with release mechanism (528) described above, release mechanism (670) of the present example is used to selectively hold spring (620) in a biased or compressed configuration. Release mechanism (670) can therefore be used to selectively release internal components of marker delivery device (600) to deploy marker (300).

Unlike marker delivery device (500) described above, marker delivery device (600) of the present example is configured to couple to a proximal end of a biopsy device (340) in place of tissue sample holder (380). Although marker delivery device (600) is shown as being used in connection with biopsy device (350), it should be understood that marker delivery device (600) may be used with a variety of alternative biopsy devices. One or more features of such biopsy device may be configured in accordance with the teachings of US Pub. No. 2018/0221002, entitled "Biopsy System," published on Aug. 9, 2018, the disclosure of which is incorporated by reference herein.

Marker delivery device (600) includes a coupler (678) to facilitate coupling marker delivery device (600) to biopsy device (340). Similar to tissue sample holder (380), coupler (678) includes an annular ring (632) and a pair of latching features (636). Additionally, coupler (678) has a distal face (634). Marker delivery device (600) may be thus coupled to proximal end of probe (320) in similar fashion as tissue sample holder (380). For instance, latching features (636) may be aligned with pins (314) on a manifold ring (318). Annular ring (632) is moved longitudinally over manifold ring (318) until distal face (634) engages a proximal face (316) of probe (330). Marker delivery device (600) is then rotated to a locked position. In the locked position, latching features (636) engage pins (314) and retain the marker delivery device (600) in a bayonet mount fashion.

Once marker delivery device (600) is coupled to a suitable biopsy device, marker delivery device (600) can be used to deploy a marker using a procedure similar to the deployment procedure described above with respect to marker delivery device (500). For instance, release mechanism (670) may be actuated to release internal structures and/or components similar to rack stowage drum (518). As similarly discussed above, such internal structures and/or components may be biased by spring (620) such that release via release mechanism (670) may result in movement of such structures and/or components. Once release mechanism (670) is actuated, structures similar to flexible push rod (516) may be driven by internal components, resulting in such structures being driven distally through an aperture or opening in distal face (684). Such structures similar to flexible push rod (516) may then translates through biopsy device (340) and into needle (390) for deployment of marker (300).

C. Dual Gear Marker delivery Device

Figure 16:
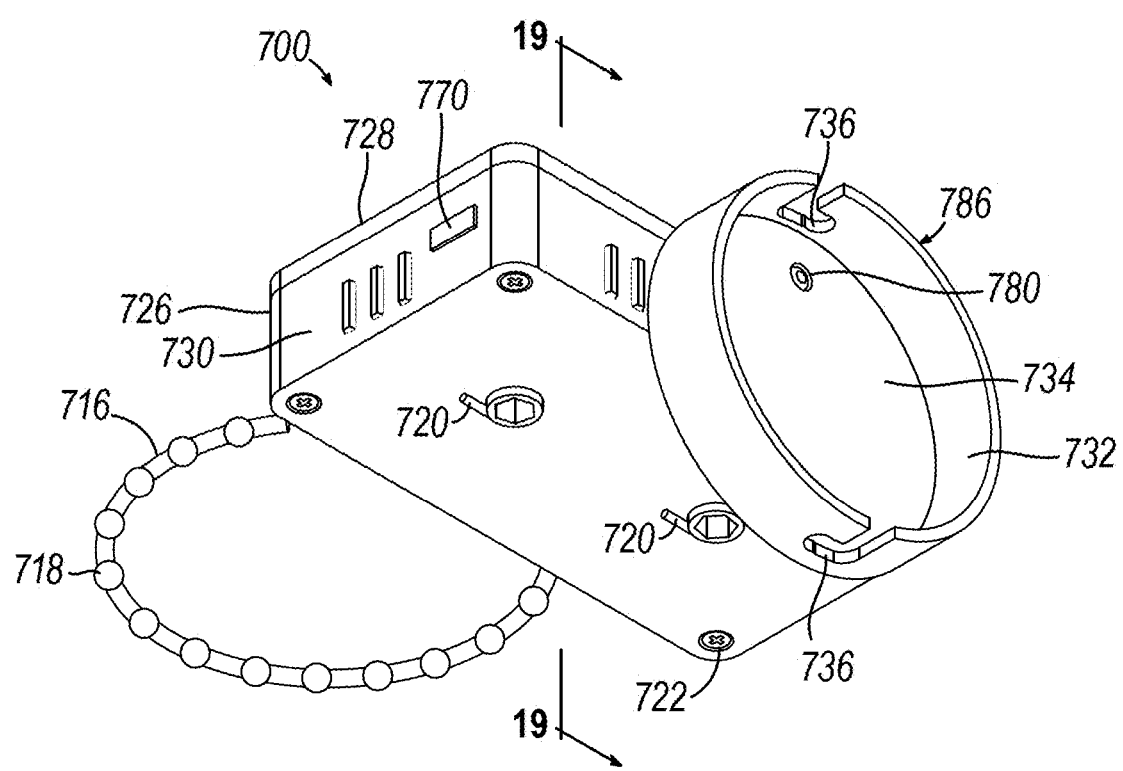
FIG. 16 depicts a perspective view of yet another exemplary marker delivery device.
Figure 17:
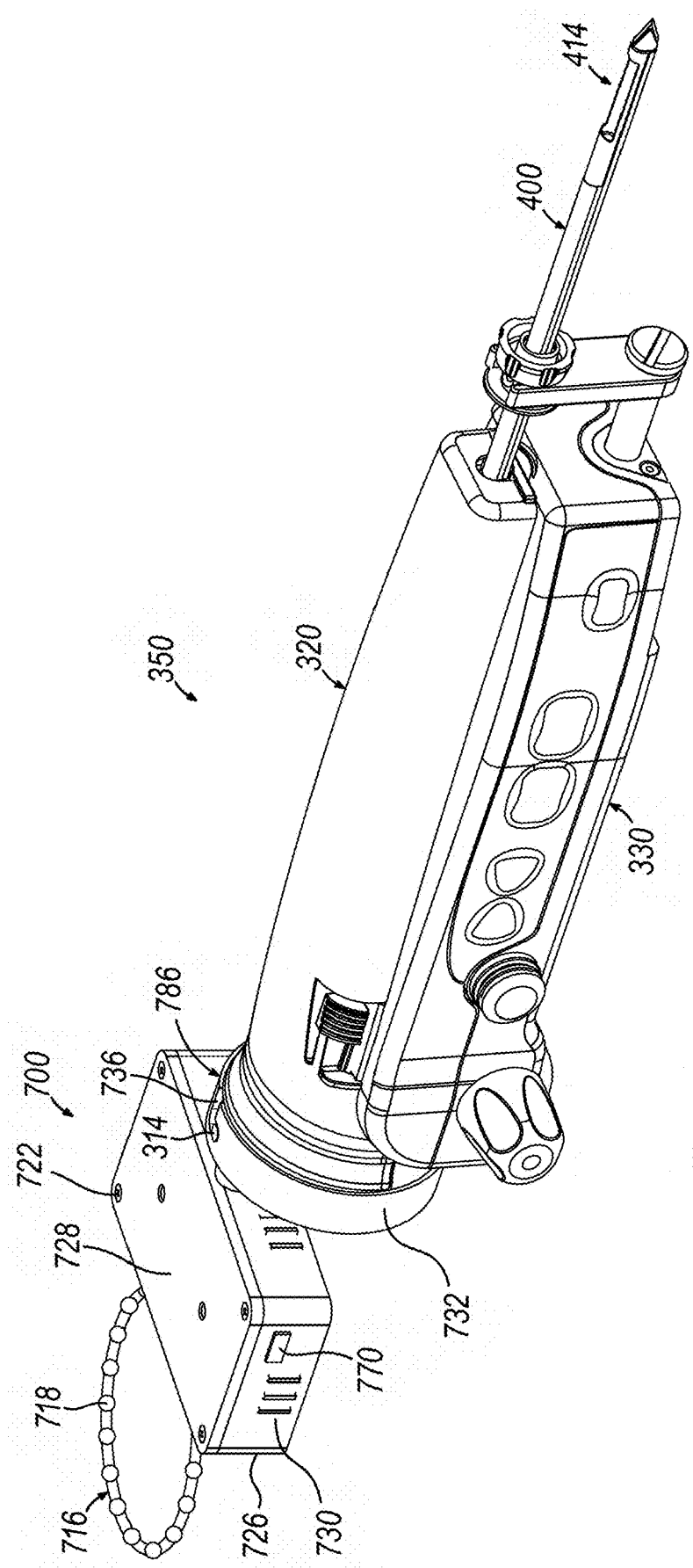
FIG. 17 depicts a perspective view of the marker delivery device of FIG. 16 coupled to the biopsy device of FIG. 5.
Figure 18:
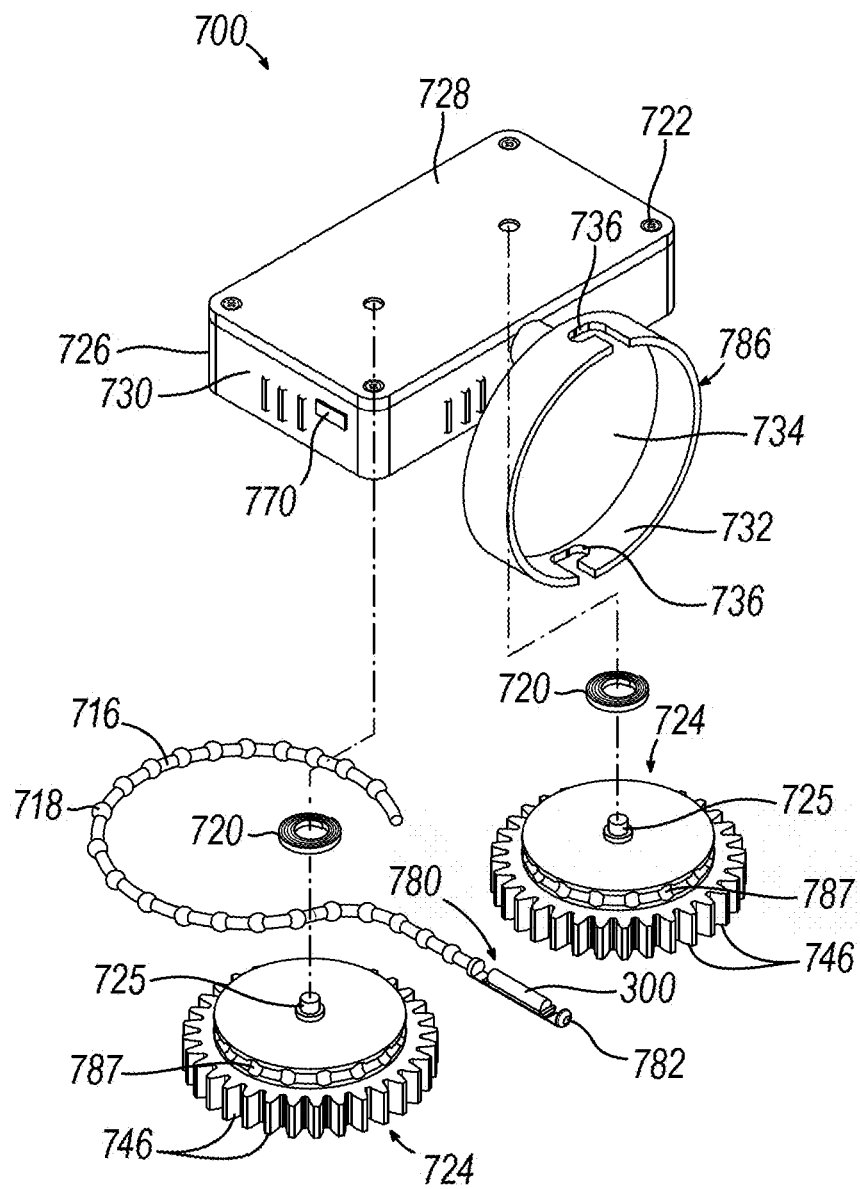
FIG. 18 depicts an exploded perspective view of the marker delivery device of FIG. 16.

FIGS. 16-18 show another exemplary marker delivery device (700) that is substantially similar to marker delivery device (600) discussed above unless otherwise explicitly noted. Like marker delivery device (600), marker delivery device (700) of the present example is configured to couple to a proximal end of a biopsy device (340) in lieu of tissue sample holder (380). FIG. 16 shows marker delivery device (700) in isolation; while FIG. 17 shows marker delivery device (700) coupled to proximal end of biopsy device (340) in lieu of tissue sample holder (380). As discussed above, in some examples, biopsy device (340) may be configured to rotate one or more portions of tissue sample holder (380) with a motor via gripping member (312). In some examples, gripping member (312) may be configured to also drive one or more portions of marker delivery device (700) when marker deliver device (700) is coupled to biopsy device (340) in lieu of tissue sample holder (380). Alternatively, and as discussed in greater detail below, marker delivery device (700) may be driven entirely independently of biopsy device (340).

As best seen in FIG. 16, marker delivery device (700) includes a housing defined by a rectangular portion (726), a lid (728) and a body (730). Rectangular portion (724) is generally rectangular in shape but may be any suitable shape configured to house various internal components of marker delivery device (700) as will be described in greater detail below. Lid (728) and body (730) are fitted together with any suitable fastener (722) such as rivets, screws, or bolts. Lid (728) and body (730) can also be fused with welding.

The housing of marker delivery device (700) further includes a coupler (786) extending distally from body (730). Coupler (786) is substantially similar to coupler (678), described above, in that coupler (786) is configured to couple marker delivery device (700) to probe (330) of biopsy device (340) in lieu of tissue sample holder (380). Similar to coupler (678) described above, coupler (786) of the present example includes an annular ring (732) and a pair of latching features (736). Additionally, coupler (786) has a distal face (734) recessed within annular ring (732). Marker delivery device (700) may be thus coupled to proximal end of probe (320) in similar fashion as marker delivery device (600) and/or tissue sample holder (380) described above. For instance, latching features (736) may be aligned with pins (314) on manifold ring (318). Annular ring (732) is moved longitudinally over manifold ring (318) until distal face (734) engages proximal face (316) of probe (330). Marker delivery device (700) may then be rotated to a locked position. In the locked position, latching features (736) engage pins (314) and retain the marker delivery device (700) in a bayonet mount fashion As best seen in FIG. 18, marker delivery device (700) further includes a flexible push rod (716), a spring (720), a release mechanism (770) and gears (724). As will be described in greater detail below, spring (720), release mechanism (770), and gears (724) are configured to operate cooperatively to drive flexible push rod (716) for deployment of marker (300) via flexible push rod (716). As will be described in greater detail below, each spring (720) is operatively coupled to a corresponding gears (724) to drive rotation of the corresponding gear (724). Such rotation of gears (724) may then drive flexible push rod (716) for deployment of maker (300).

Release mechanism (770) is configured to release one or both gear (724). In other words, release mechanism (770) is generally configured to selectively hold one or both gears (724) with each spring (720) in a biased or compressed configuration. Release mechanism (770) is further configured as a push button mechanism such that actuation of a button can be used to release gears (724) and initiate rotation thereof via each spring (720). Although release mechanism (770) of the present example is configured as a push button mechanism, it should be understood that in other examples, a variety of other selective engagement mechanisms may be used as will be understood by those of ordinary skill in the art in view of the teachings herein.

As best seen in FIG. 18, each gear (724) includes an axil (725), a drive surface in the form of a beaded drive surface (787), and a plurality of gear teeth (746). Axil (725) of each gear (724) is configured engage a portion of the housing such as lid (728) to provide rotation of each gear (724) within the housing about a fixed axis. Although not shown, it should be understood that in some examples each axil (725) may associated with a bearing or other friction reducing component.

Each beaded drive surface (787) extends around an outer perimeter of a corresponding gear (724). Each beaded drive surface (787) is generally configured to engage a portion of flexible push rod (716). As will be described in greater detail below, such engagement between each beaded drive surface (787) and flexible push rod (716) is configured to transfer rotatory motion of each gear (724) into translation of flexible push rod (716). As such, it should be understood that each gear (724) is positioned within body (730) such that each beaded drive surface (787) is separated from the opposite beaded drive surface (787) a distance approximately equivalent to the diameter of flexible push rod (716).

Each gear (724) further includes a plurality of gear teeth (746) proximate a corresponding beaded drive surface (787). Gear teeth (746) are also positioned around the outer perimeter of each gear (724) and extend radially outwardly from a corresponding beaded drive surface (787). Such a radial extension for gear teeth (746) is configured such that gear teeth (746) of one gear (724) may engage corresponding gear teeth (746) of the opposite gear (724). In other words, gear teeth (746) of one gear (724) are configured to mesh with gear teeth (746) of the other gear (724).

This meshing relationship between gear teeth (746) permits one gear (724) to drive another. In some examples, this meshing relationship can be used to maintain synchronized rotation between gears (724). In addition, or in the alternative, in some examples, this meshing relationship can be used such that only a single spring (720) can be used to rotate one gear (724), while the other gear (724) is rotated by rotation of the gear (724) associated with the single spring (720). Additionally, although not shown, it should be understood that in some examples, gear teeth (746) can mesh with a drive train or other components so that springs (720) can be omitted entirely with gears (724) being rotated by an external power source (e.g., gripping member (312) of biopsy device (340)).

Figure 19:
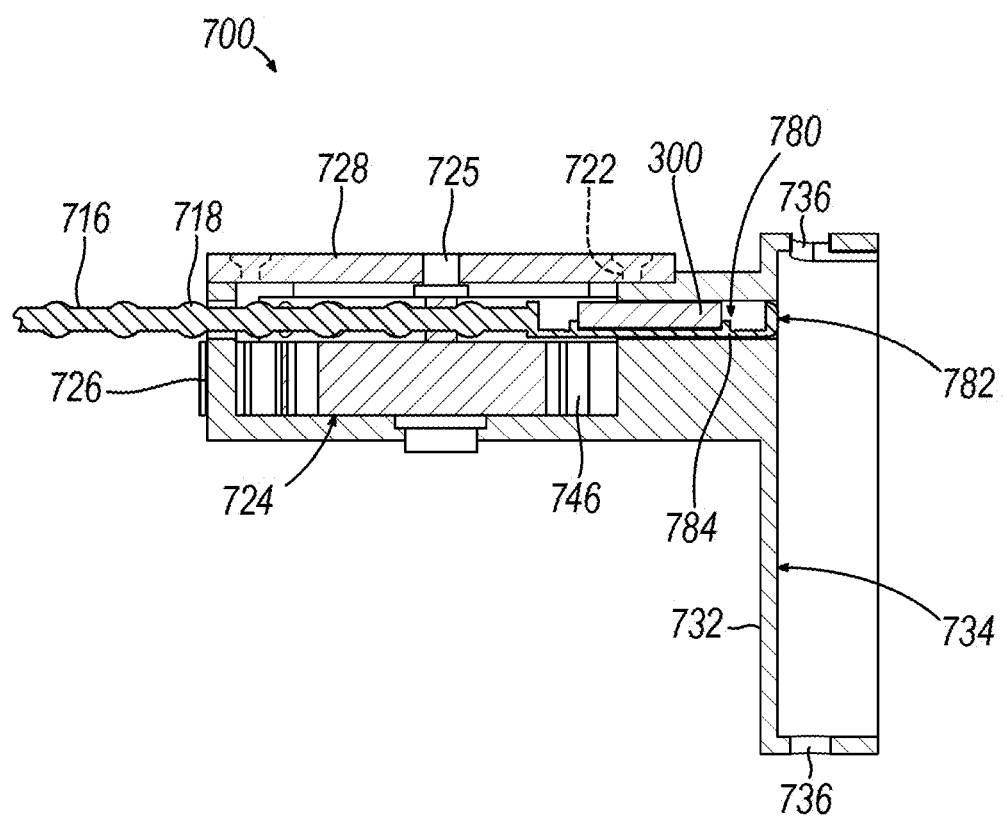
FIG. 19 depicts a perspective cross-sectional view of the marker delivery device taken along line 19-19 of FIG. 16.
Figure 20:
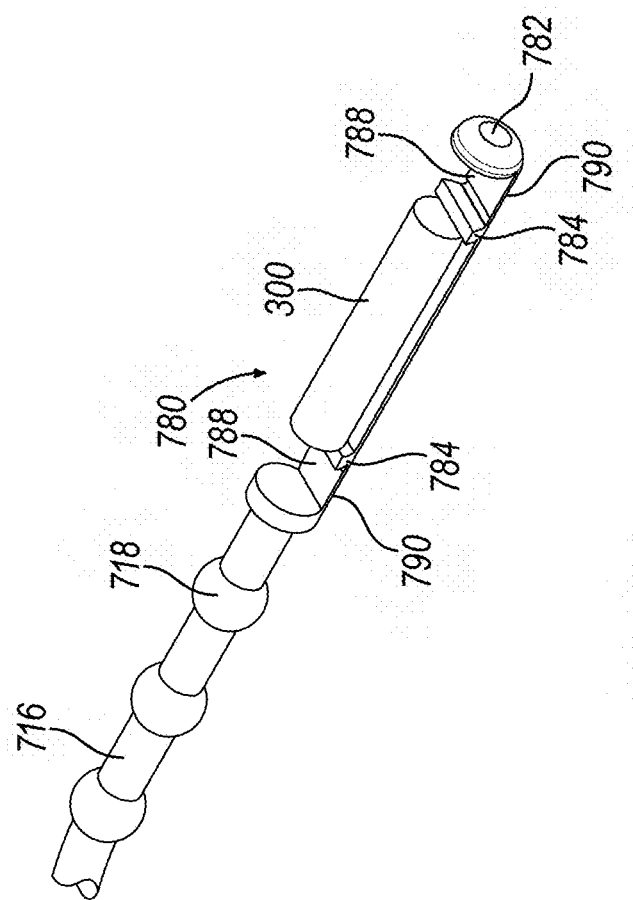
FIG. 20 depicts an enlarged perspective view of a distal portion of a beaded cable of the marker delivery device of FIG. 16.

As best seen in FIGS. 19 and 20, flexible push rod (716) includes a drive portion defined by a plurality of beads (718). As such, flexible push rod (716) may be referred to as a flexible beaded rod in some examples. Beads (718) are generally configured to provide an irregular drive surface, which can be engaged by beaded drive surface (787) to move flexible push rod (716). Each bead (718) comprises a protrusion having a generally spherical shape. In other examples, each bead (718) can have a variety of alternative shapes such as oval-shaped, square-shaped, rectangular-shaped, elliptical-shaped, and/or etc. Additionally, although each bead (718) is shown as a protrusion in the present example, it should be understood that in other examples, the configuration of each bead (718) can be readily reversed and instead be an indentation.

Regardless of the particular configuration of each bead (718), it should be understood that beaded drive surface (787) of each gear (724) is generally configured to correspond to the particular shape of each bead (718). Thus, in the present example, beaded drive surface (787) includes a plurality of indentations corresponding to the particular shape of each bead (718). Of course, in examples where the particular shape of each bead (718) is varied, the particular shape of beaded drive surface (787) may likewise be varied.

Beads (718) are arranged along a length of flexible push rod (716) at equal intervals. Corresponding indentations in beaded drive surface (787) likewise are spaced at equal intervals corresponding to the spacing used in flexible push rod (716). With such correspondence, flexible push rod (716) may be received between gears (724) and each beaded drive surface (787) may engage one or more beads (718). Rotation of gears (724) may then drive beads (718), and thus flexible push rod (716), in the direction of rotation of gears (724). As gears (724) rotate, additional beads (718) may become engaged by beaded drive surface (787), while other beads (718) become disengaged. Thus, beaded drive surface (787) and beads (718) are configured to operate similarly to gear teeth in meshing gears.

As best seen in FIG. 20, flexible push rod (716) further includes a deployer tip (780) defined by a distal end of flexible push rod (716). Deployer tip (780) includes a pair of living hinges (784), which are generally configured to convert axial movement of flexible push rod (716) into lateral movement of a portion of deployer tip (780) for deployment of marker (300). Each living hinge (784) is generally formed of any suitable material known in the art having resilient properties. Each living hinge (784) also has a flexed and unflexed position. Each living hinge (784) is shown in the unflexed position. A flat upper portion (788) and an arcuate bottom portion (790) is positioned between each living hinge (784). Flat upper portion (788) and arcuate bottom portion (790) are configured to transition living hinge (784) from the unflexed position to the flexed position. As can be seen, living hinges (784), flat upper portion (788) and arcuate bottom portion (790) all lay flat when in the unflexed position.

To transition from the unflexed position to the flexed position, a distal tip (782) of deployer tip (780) may contact a distal structure of a needle similar to needle (400). This contact may prevent movement of distal tip (782), while flexible push rod (716) continues to move distally, accumulating tension within flexible push rod (716). Once a sufficient amount of tension is accumulated, living hinges (784) will buckle and push flat upper portion (788) and arcuate bottom portion (790) upwardly to deploy marker (300).

D. Exemplary Driven Marker delivery Device

Figure 21:
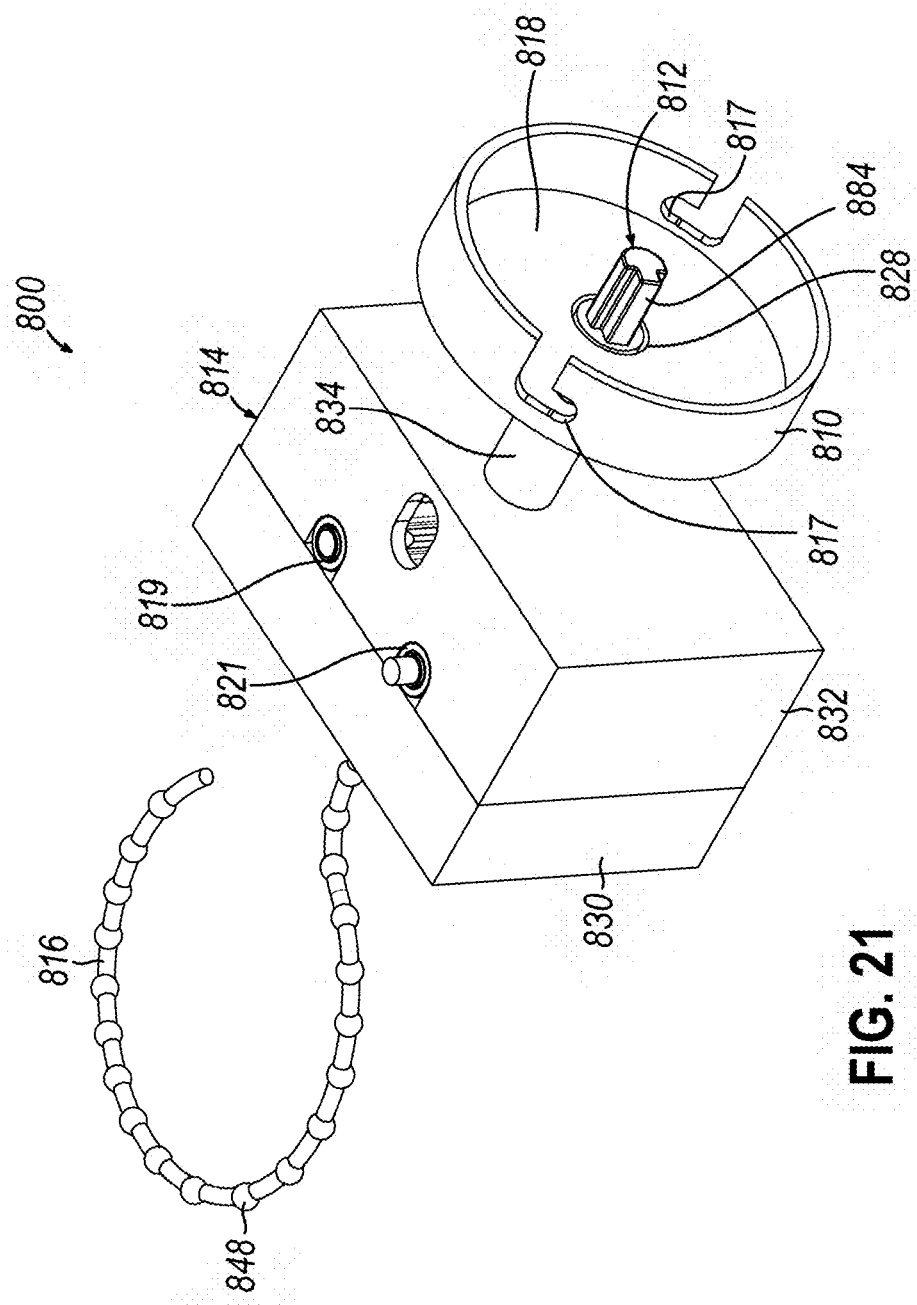
FIG. 21 depicts a perspective view of still yet another exemplary marker delivery device.
Figure 22:
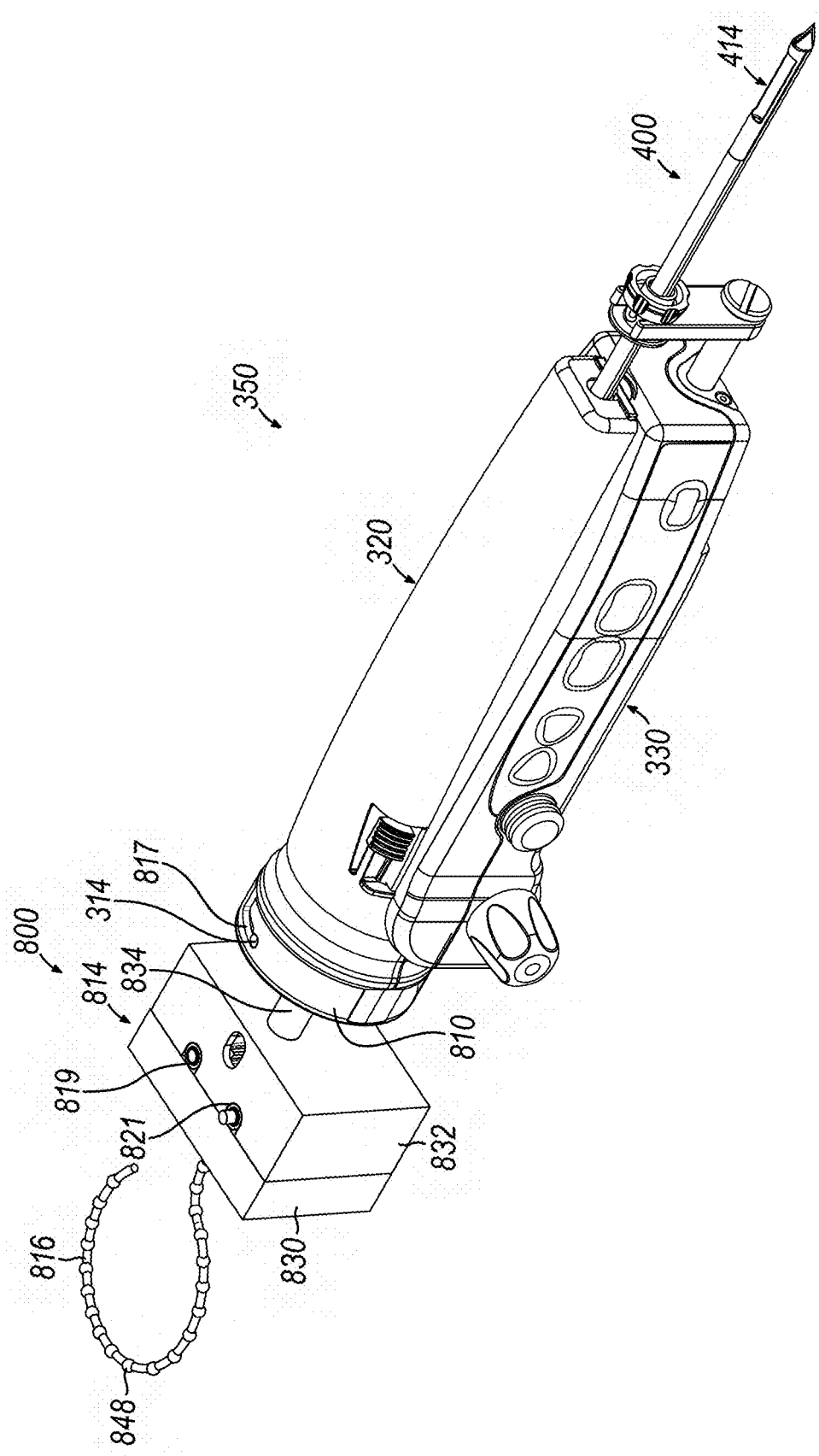
FIG. 22 depicts a perspective view of the marker delivery device of FIG. 21 coupled to the biopsy device of FIG. 5.
Figure 23:
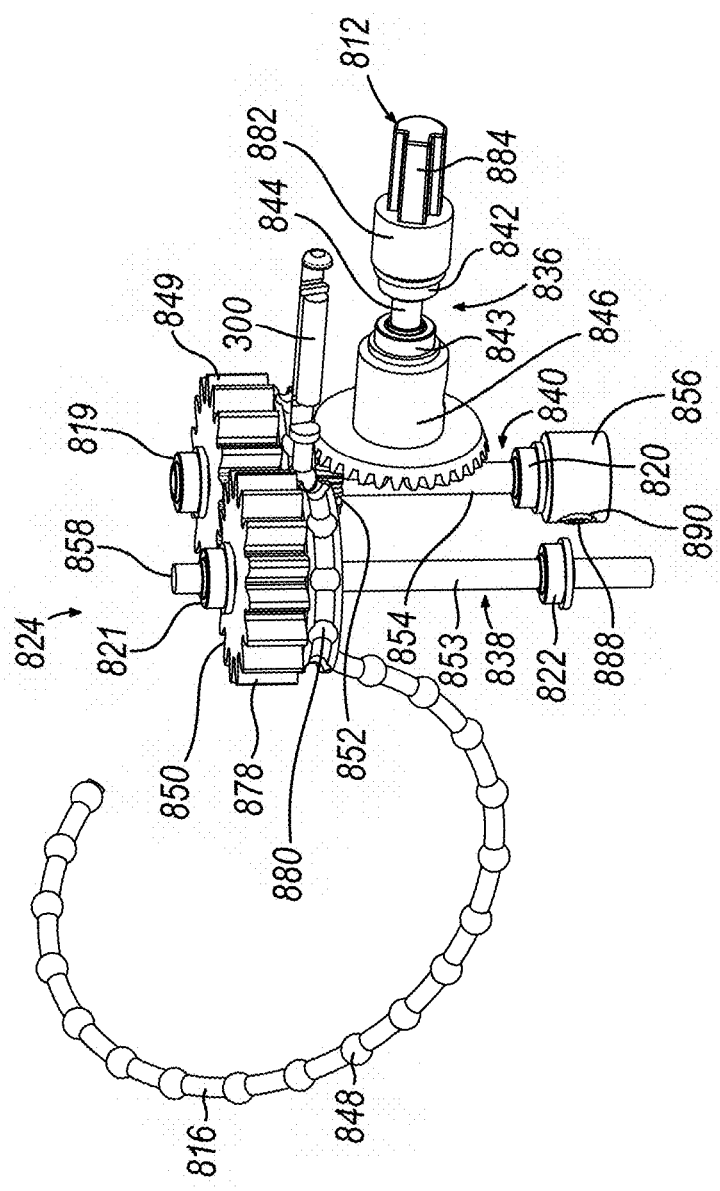
FIG. 23 depicts a perspective view of a gear assembly of the marker delivery device of FIG. 21.

FIGS. 21-23 show another marker delivery device (800) that is configured to be coupled to a proximal end of a biopsy device (340) in lieu of tissue sample holder (380). FIG. 21 shows marker delivery device (800) in isolation; while FIG. 22 shows marker delivery device (800) coupled to biopsy device (340) in lieu of tissue sample holder (380). As described above, in some examples biopsy device (340) is configured to drive rotation of one or more components of tissue sample holder (380) via gripping member (312). As will be described in greater detail below, marker delivery device (800) of the present example is generally configured to use such functionality to drive portions thereof.

Marker delivery device (800) is substantially similar to marker delivery device (700) described above. For instance, marker delivery device (800) includes a housing (814) having a proximal housing portion (830), a distal housing portion (832), and an elongate portion (834). Housing (814) is constructed of any suitable rigid material known in the art such as plastic, aluminum, or stainless steel. Proximal housing portion (830) and distal housing portion (832) are fitted together with any suitable fastener such as rivets, screws, or bolts. Proximal housing portion (830) and distal housing portion (832) may also be fused with welding. Distal housing portion (832) is operatively fixed to elongate portion (834) that extends distally from distal housing portion (832).

Housing (814) further includes an annular ring (810) disposed on a distal end of elongate portion (834). Annular ring (810) is similar to annular ring (732) of marker delivery device (700) described above. For instance, as with annular ring (732) described above, annular ring (810) of the present example is configured to fasten to a portion of biopsy device (840), such as probe (330), in lieu of tissue sample holder (380). As with annular ring (732) described above, annular ring (810) of the present example includes a distal face (818) and a pair of latching features (817). As similarly discussed above, latching features (817) are configured to receive pins (314) of biopsy device (340) to selectively couple marker delivery device (800) to biopsy device (340).

A longitudinal shaft adaptor (812) (also may be referred to as a coupling shaft) extends distally from distal face (818). As will be described in greater detail below, longitudinal shaft adaptor (812) is configured to engage a portion of biopsy device (340), such as gripping member (312) to drive movement of various components of marker delivery device (800) disposed within housing (814). As such, it should be understood that longitudinal shaft adaptor (812) is centrally located within annular ring (810) for engagement with gripping member (312) of biopsy device (340).

Figure 24:
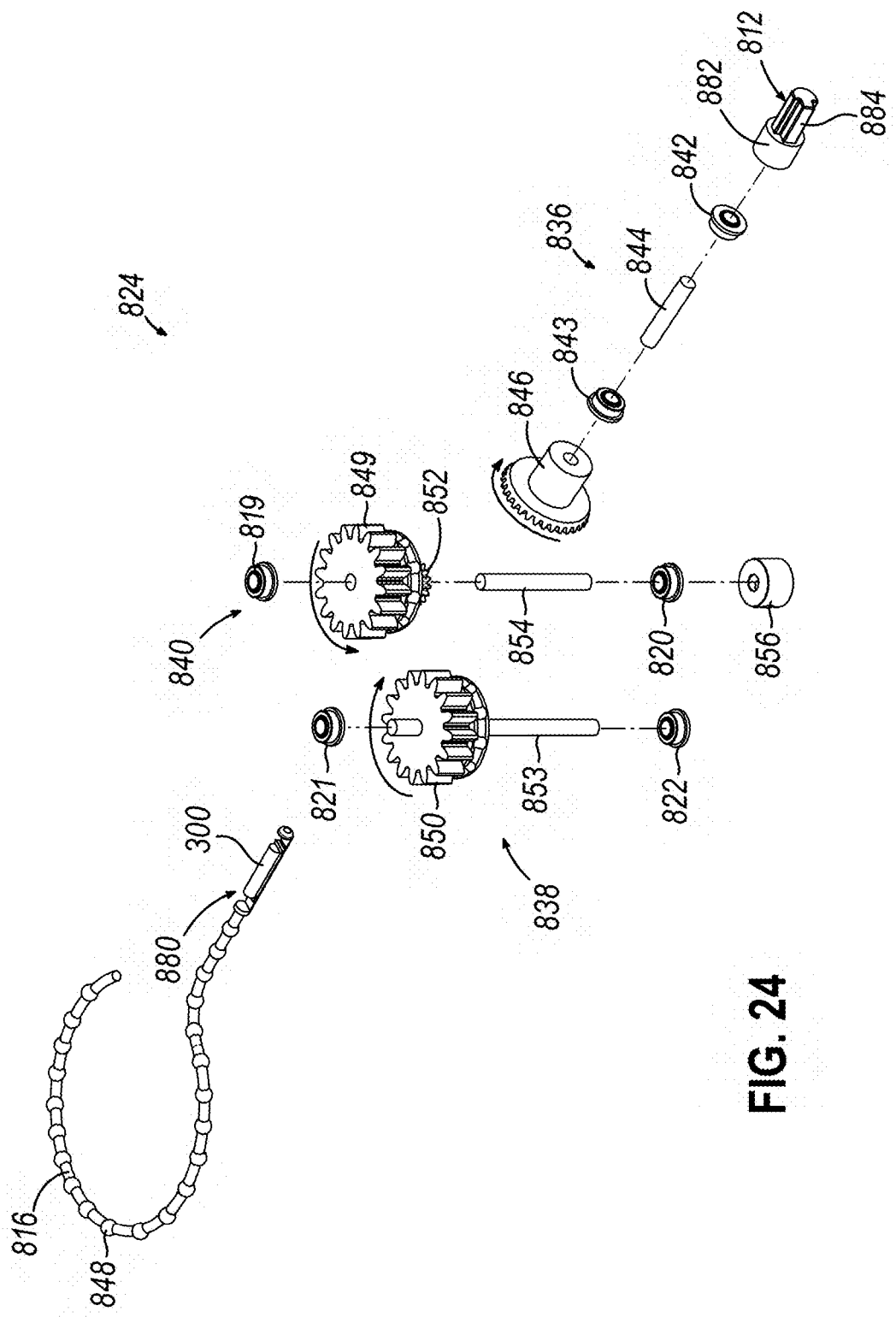
FIG. 24 depicts an exploded perspective view of the gear assembly of FIG. 23.

The interior of housing (814) is shown in greater detail in FIGS. 23 and 24. As can be seen, housing (814) contains a gear assembly (824) and a flexible push rod (816). Gear assembly (824) includes a longitudinal shaft assembly (836), an idler shaft assembly (838), and a drive shaft assembly (840). Drive shaft assembly (840) and idler shaft assembly (838) are fitted between proximal housing portion (830) and distal housing portion (832). At least a portion of longitudinal shaft assembly (836) is laterally disposed within elongate housing portion (834).

FIG. 24 shows assemblies (836, 838, and 840) in greater detail. As can be seen, longitudinal shaft assembly (836) extends proximally within housing (814) from distal face (818). Longitudinal shaft assembly (836) includes longitudinal shaft adapter (812), a first bearing (842), a second bearing (843), a longitudinal shaft (844), and a longitudinal bevel gear (846). As noted above, longitudinal shaft adapter (812) is configured to slidably couple to gripping member (312) of biopsy device (340). A proximal end of longitudinal shaft adapter (812) is operatively coupled to longitudinal shaft (844) such that longitudinal shaft adaptor (836) is configured to communicate rotatory motion to longitudinal shaft (844).

Longitudinal shaft (844) extends proximally from longitudinal shaft adapter (812) through bearings (842, 843). In particular, first bearing (842) is disposed in distal end of elongate portion (834) of housing (814), and second bearing (843) is disposed in proximal end of elongate portion (834) of housing (814).

Longitudinal bevel gear (846) is located on proximal end of longitudinal shaft (844). Thus, longitudinal shaft (844) is configured to communicate rotary motion from longitudinal shaft adapter (812) to longitudinal bevel gear (846) to rotate longitudinal bevel gear (846). As will be described in greater detail below, longitudinal bevel gear (846) is generally configured to rotate to drive movement of various portions of marker delivery device (800) and thereby drive movement of flexible push rod (816).

Drive shaft assembly (840) includes a third bearing (819), a drive gear (849), a drive bevel gear (852), a drive shaft (854), a fourth bearing (820), and a shaft collar (856). Drive shaft assembly (840) is arranged transverse to longitudinal shaft assembly (836). Third bearing (819) is disposed between top of proximal housing portion (830) and top of distal housing portion (832). Drive shaft (854) is axially fixed, but remains rotatable via third bearing (819). Drive gear (849) is affixed to drive shaft (854), below third bearing (819). Drive bevel gear (852) is affixed to drive shaft (854) below drive gear (849). Alternatively, drive bevel gear (852) may be disposed within drive gear (849). Fourth bearing (820) is disposed between bottom of proximal housing portion (830) and bottom of distal housing portion (832). Drive shaft extends distally through bottom of housing (814). Shaft collar (856) is affixed to a portion of drive shaft (854) that extends from bottom of housing (814).

Idler shaft assembly (838) has a fifth bearing (821), an idler gear (850), an idler shaft (853), and a sixth bearing (822). Idler shaft assembly (838) is arranged transverse to longitudinal shaft assembly (836). Fifth bearing (821) is disposed between top of proximal housing portion (830) and top of distal housing portion (832). Idler shaft (853) is affixed to inside of fifth bearing (821). Idler gear (850) is affixed to idler shaft (853), below fifth bearing (821). Sixth bearing (822) is disposed between bottom of proximal housing portion (830) and bottom of distal housing portion (832). Idler shaft (853) extends distally through bottom of housing (814).

Longitudinal shaft adapter (812) protrudes through longitudinal aperture (828) disposed in distal face (see FIG. 21). Longitudinal shaft adapter (812) is configured to be rotatably coupled to gripping member (312). In particular, longitudinal shaft adapter (812) includes a coupler (882) and a mating shaft (884). Coupler (882) is configured to be affixed to distal end of longitudinal shaft (844). Mating shaft (884) has a generally arcuate shape. Mating shaft (884) is configured to be mated with gripping member (312) of biopsy probe (320). As such, it should be understood that mating shaft (884) of the present example includes a keyed configuration. Although a particular keyed configuration for mating shaft (884) is shown, it should be understood that in other examples various alterative configurations may be used such as square-shaped, triangular-shaped, hex-shaped, and/or etc.

Gripping member (312) couples to longitudinal shaft adapter (812), similar to how gripping member (312) couples to manifold shaft (334) to rotate tissue sample holder (380). Further discussion of how gripping member (312) is rotated by a motor (not shown) is discussed above. In operation, gripping member (312) rotates longitudinal shaft adapter (812). Longitudinal shaft adapter (836) rotates longitudinal shaft (844). Longitudinal shaft (844) rotates longitudinal bevel gear (846). Longitudinal bevel gear (846) engages drive bevel gear (852) and rotates drive bevel gear (852). Drive bevel gear (852) rotates drive shaft (854) and drive gear (849). Drive shaft (854) rotates drive gear (849). Drive gear (849) engages idler gear (850) and rotates idler gear (850). Drive gear (849) and idler gear (850) engages beads (848) of flexible push rod (816) translating flexible push rod (816) through a rod aperture in distal face (818) and into needle (400) of biopsy device (340).

Longitudinal shaft (844) rotates in a clockwise direction when viewed from the distal face (824) (see FIG. 21). Drive gear (849) rotates in a counterclockwise direction when viewed from a top of housing (814). Idler gear (850) rotates in a clockwise direction when viewed from top of housing (814). The direction of rotation can be reversed with longitudinal shaft (844) rotating in a counterclockwise direction, the drive gear (849) rotating in a clockwise direction, and idler gear (850) rotating in a clockwise direction.

E. Marker Delivery Device Flexible Push Rod with Living Hinge Deployer Tip

Figure 25:
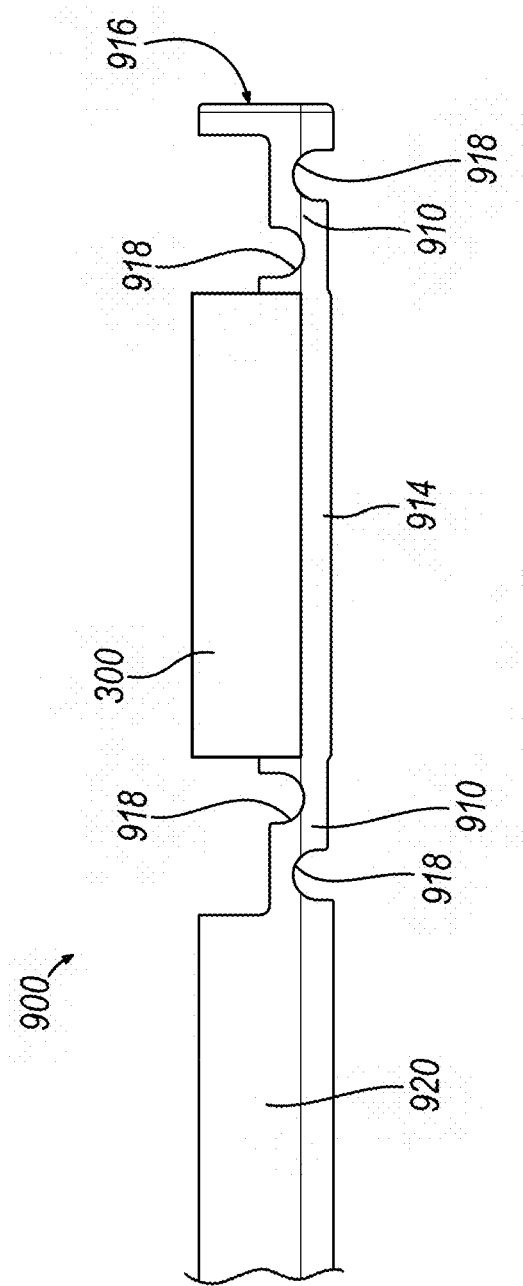
FIG. 25 depicts a side cross-sectional view of an exemplary living hinge that can be readily incorporated into the marker delivery device of FIG. 21.

FIG. 25 shows a deployer tip (900) extending distally from a flexible push rod (920). Deployer tip (900) can be used with any of above marker delivery devices (500, 600, 700, 800). Thus, push rod (920) of the present example may be readily substituted with any one or more of push rods (516, 716, 816). Although deployer tip (900) is shown herein as being generally integral with flexible push rod (920), it should be understood that in other examples, deployer tip (900) and flexible push rod (920) may be separate components coupled together by any suitable means.

Deployer tip (900) is generally configured to deploy a marker such as marker (300) laterally or perpendicularly from the longitudinal axis of flexible push rod (920) using a buckling action. To facilitate such functionality, deployer tip (900) includes a pair of living hinges (910) separated by a flat portion (914), and a distal face (916). Each living hinge (910) includes a plurality of arcuate half bores (918) located proximate flat portion (914). Half bores (918) are generally configured to narrow the cross-section of each living hinge (910) to promote flexibility of each living hinge (910). Half bores (918) are further configured to provide clearance or space for movement of each living hinge (910) during deployment of a marker similar to marker (300), as will be described in greater detail below.

Flat portion (914) is configured to provide a generally flat section for a marker such as marker (300) to rest upon. In other words, flat portion is configured to hold marker (300) or other markers. Although flat portion (914) of the present example is shown as being used with marker (300), it should be understood that various alternative markers may be readily used with flat portion (914). Optionally, flat portion (914) may include one or more locating features to hold marker (300) in a specific position on flat portion (914) until deployment occurs. By ways of example only, suitable locating features may include steps, detents, rounds, ribs, and/or etc.

Deployer tip (900) is generally formed of a resilient material such as rubber or plastic. Alternatively, any suitable material known in art having resilient properties can be used to form deployer tip (900). For ease of manufacturability, deployer tip (900) of the present example is shown as being of an isotropic or single material construction. However, it should be understood that in other examples, deployer tip (900) may comprise a composite of one or more different materials. Such configurations may be desirable to provide different properties within different parts of deployer tip (900). For instance, in some examples flat portion (914) may be rigid, while each living hinge (910) is flexible.

Figure 26:
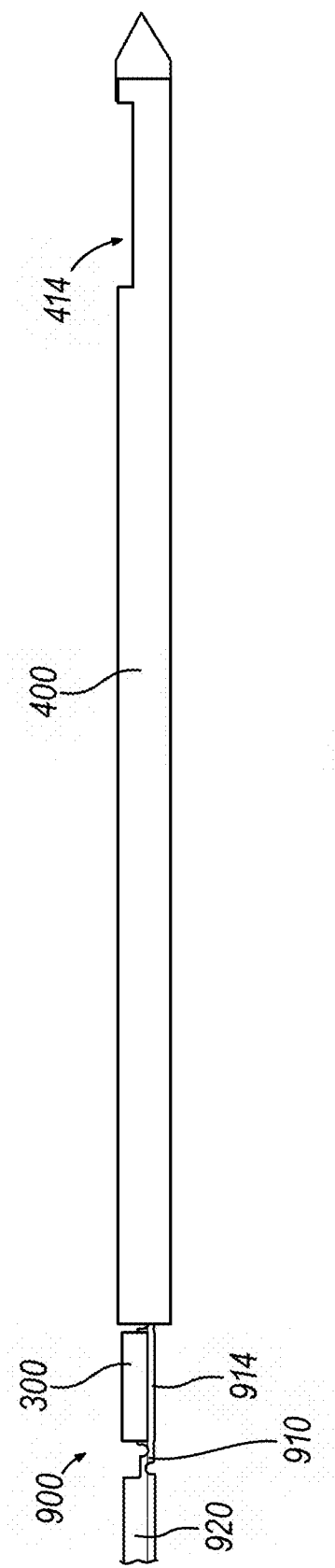
FIG. 26 depicts a side cross-sectional view of the living hinge of FIG. 25 being inserted into a biopsy marker needle.

Each living hinge (910) has an unflexed position and a flexed position. In FIG. 25, living hinge (910) is shown in the unflexed position. With living hinge (910) in the unflexed position, deployer tip (900) may be configured for insertion into a component such as needle (400). In particular, as seen in FIG. 26, flexible push rod (920) may used for insertion of deployer tip (900) within a proximal end of needle (400) of biopsy device (340) while each living hinge (910) is in the unflexed position.

Figure 27:
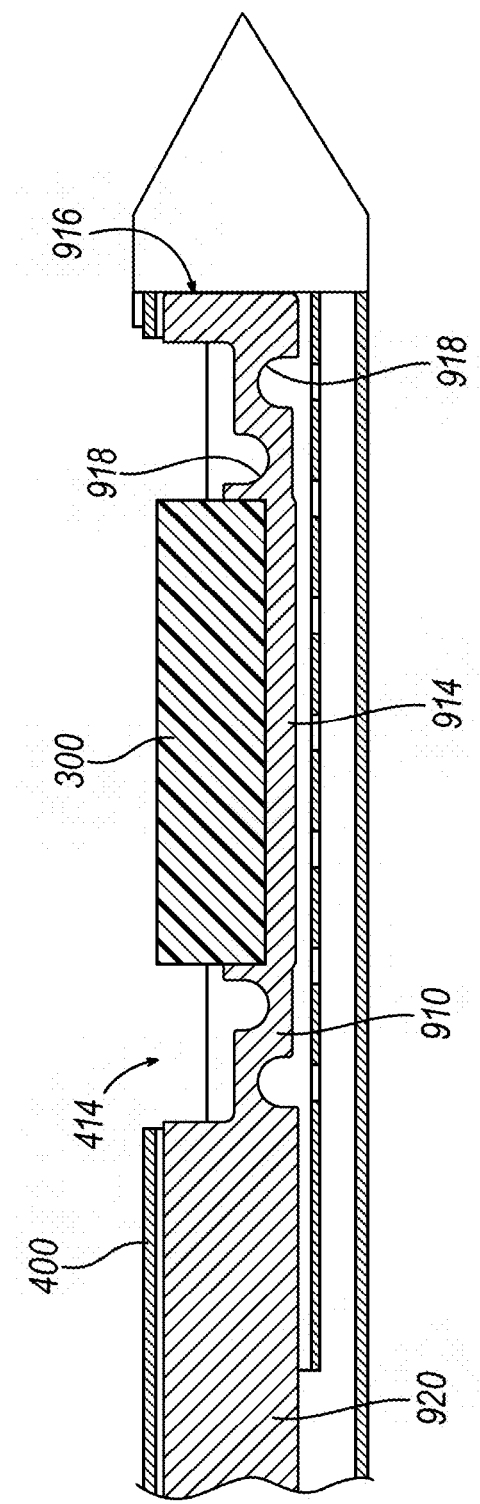
FIG. 27 depicts a side cross-sectional view of the living hinge partially inserted into the biopsy marker needle with the living hinge in a relaxed state.

FIG. 27 shows deployer tip (900) insertion into needle (400), but prior to deployment. At this stage, each living hinge (910) remains in the unflexed position. Once deployer tip has been distally translated, distal face (916) may engage a portion of needle (400) such as a proximal face of the interior of needle (400).

Once distal face (916) engages needle (400), further advancement of flexible push rod (920) distally applies a compressive force to deployer tip (900). Once a sufficient amount of force is applied, each living hinge (910) will buckle or otherwise permit movement of flat portion (914) laterally. As a result, this transitions each living hinge (910) from the unflexed position to the flexed position. During this transition, at least some deformation of living hinges (910) may occur. For instance, arcuate half bores (918) may straighten in some examples.

Figure 28:
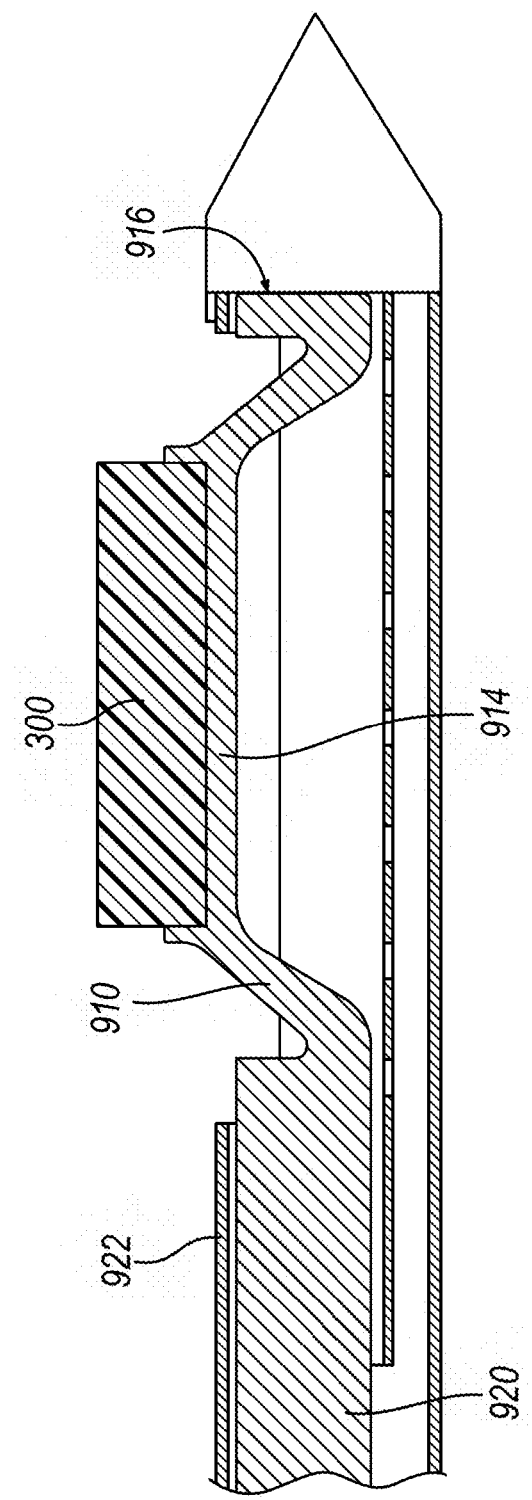
FIG. 28 depicts a side cross-sectional view of a living hinge fully inserted into the biopsy marker needle with the living hinge in a biased state.

FIG. 28 shows each living hinge (910) after transition to the flexed position. As can be seen, the straightened arcuate half bores (918) raise or laterally move flat portion (914). This lateral movement of flat portion (914) causes marker (300) to likewise move laterally and be deployed into the patient's body through lateral aperture (414) of needle (400).

IV. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A marker delivery device comprising: a housing; an elongate flexible push rod including a first transverse drive surface and a deployer tip, the deployer tip being configured to receive a biopsy site marker; and a first wheel having a second transverse drive surface, wherein the first transverse drive surface is configured to be driven by the second transverse drive surface to translate the flexible push rod distally.

Example 2

The marker delivery device of Example 1, further comprising a first shaft, wherein the first shaft is configured to rotatably couple the first wheel to the housing; and a spring, wherein the spring includes a first end and a second end, wherein the first end is coupled to the shaft and the second end is coupled to the first wheel, and the second end is coupled to the housing, wherein the spring has a biased position and a relaxed position, wherein in the spring in the biased position is configured to be under tension, and in the relaxed position spring is configured to rotate the first wheel and translate flexible push rod in a coordinated linear and rotational movement through the cannula to deploy the marker through the lateral aperture.

Example 3

The marker delivery device of Example 2 further comprising a second wheel having a third transverse drive surface, wherein the third transverse drive surface engages the first transverse drive surface to support the flexible push rod in the transverse direction relative to the flexible push rod.

Example 4

The marker delivery device of Example 3 further comprising a third wheel having a fourth transverse drive surface, wherein the fourth transverse drive surface engages the third transverse drive surface configured to hold the second wheel stationary in the biased position.

Example 5

The marker delivery device of any one or more of Examples 2 or 3, further comprising a release mechanism, wherein the release mechanism is configured to removably couple to the first transverse drive surface, wherein the release mechanism is configured to hold the spring in the biased position, and release the tension in the spring to transition the spring from the biased position to the relaxed position.

Example 6

The marker delivery device of any one or more of Examples 2 or 3, further comprising a release mechanism, wherein the release mechanism is configured to removably couple to the second transverse drive surface, wherein the release mechanism is configured to hold the spring in the biased position, and release the tension in the spring to transition the spring from the biased position to the relaxed position.

Example 7

The marker delivery device of Example 3, further comprising a release mechanism, wherein the release mechanism is configured to removably couple to the third transverse drive surface, wherein the release mechanism is configured to hold the spring in the biased position, and release the tension in the spring to transition the spring from the biased position to the relaxed position.

Example 8

The marker delivery device of Example 4 further comprising a release mechanism, wherein the release mechanism is configured to removably couple to the fourth transverse drive surface, wherein the release mechanism is configured to hold the spring in the biased position, and release the tension in the spring to transition the spring from the biased position to the relaxed position.

Example 9

The marker delivery device of any one or more of Examples 1 through 8, wherein the deployer tip includes a flap having a free end and a hinged end, wherein the flap is configured to transition between an open state and a closed state, wherein the hinged end is configured to be held in the closed state by an interior surface of a biopsy needle which holds the marker within the deployer tip, and the free end is configured to rotate in an arcuate path to transition the flap to the open state when not held closed by the interior surface of the biopsy needle; a distal tip configured to engage a proximal face of a biopsy needle; a ramp configured to transversely engage a marker and translate the marker in a transverse direction relative to the biopsy needle when the distal tip engages the proximal face of biopsy needle; and a recess, wherein the recess is slidably couple to the flexible push rod, wherein the recess is configured to allow the flexible push rod to translate through the recess to engage the marker and translate the marker along the ramp.

Example 10

The marker delivery device of any one or more of Examples 1 through 9 wherein the deployer tip includes: a first living hinge constructed of a resilient material, wherein the first living hinge defines a plurality of arcuate half bores, wherein the first living hinge is configured to transition between a resting position and a flexed position; a flat portion proximal to living hinge and configured to hold a marker; and a distal tip configured to engage the proximal face of a biopsy needle to transition the first living hinge from the resting position to the flexed position.

Example 11

The marker delivery device of Example 10 wherein the deployer tip includes a second living hinge, wherein the first living hinge is located proximally in relation to the flat portion, and the second living hinge is located distally in relation to the flat portion and the second living hinge is located proximally in relation to the distal tip.

Example 12

The marker delivery device of any one or more of Examples 1 through 11, wherein the flexible push rod includes a smooth side, wherein smooth side is configured to ride on an inner surface of a biopsy needle.

Example 13

The marker delivery device of any one or more of Examples 8 through 12, wherein the first transverse drive surface, the second transverse drive surface, the third transverse drive surface, and the fourth transverse drive surface include gear teeth.

Example 14

The marker delivery device of any one or more of Examples 8 through 13 wherein the first transverse drive surface, the second transverse drive surface, the third transverse drive surface, and the fourth transverse drive surface are beaded.

Example 15

The marker delivery device of any one or more of Examples 1 through 14 further comprising a sterile lubrication administered within the housing and configured to reduce friction between an interior surface of the housing and the smooth side of the flexible push rod.

Example 16

A marker delivery device comprising: a housing; a flexible rack including a set of rack teeth and a deployer tip, a portion of the flexible rack being configured for insertion into a biopsy needle; a first gear having a set of first gear teeth, wherein the rack teeth are configured to engage the first gear teeth to translate the flexible rack distally; a first shaft, wherein the first shaft is configured to rotatably couple the first gear to the housing; a second gear having a set of second gear teeth, wherein the second gear teeth engage a rack gear; a third gear having a set of third gear teeth, wherein the third gear teeth engage the second gear teeth; a spring, wherein the spring includes a first end and a second end, wherein the spring is located on the first shaft and the first end is coupled to the first gear, and the second end is coupled to the housing, wherein the spring is configured to transition between a biased position and an unbiased position, and the spring is configured to rotate the first gear and translate the flexible rack in a coordinated linear and rotational movement to deploy a marker distally when transitioning between the biased position and the unbiased position; and a release mechanism, wherein the release mechanism is configured to removably couple to the third gear teeth and the release mechanism is configured to hold the third gear stationary in a biased position and configured to allow the third gear to rotate in a relaxed position.

Example 17

The marker delivery device of Example 16, wherein the release mechanism includes a button; an arm having a pivot point; and a dog, wherein the button is configured to engage the arm and rotate the arm around pivot point to dis-engage the dog from the third gear.

Example 18

A marker delivery device comprising: a flexible rack including a deployer tip, wherein the flexible rack is configured to deliver a marker to a biopsy site; a stowage drum configured to receive the flexible rack in a coiled configuration; a spring configured to retain potential energy; and a release mechanism configured to release the potential energy of the spring.

Example 19

The marker delivery device of Example 18, further comprising a housing, wherein the housing is configured to receive a first end of the spring, wherein the stowage drum is configured to receive a second end of the spring.

Example 20

The marker delivery device of Example 18 or 19, further comprising a coupler operable to couple to a biopsy device.

Example 21

A marker delivery device for use with a biopsy device to deploy a biopsy site marker, the marker delivery device comprising: a flexible beaded rod including a plurality of beads and a deployer tip; a first gear including a set of first gear teeth, and a first beaded drive surface; a second gear including a set of second gear teeth, and a second beaded drive surface, wherein the first gear teeth are rotatably meshed with the second gear teeth and the first beaded drive surface and the second beaded drive engages the plurality of beads to guide and support the flexible beaded rod between the two gears; and a housing including a first portion and an annular ring having a mating feature, a distal face and a flexible beaded rod aperture, wherein the mating feature is configured to be releasably coupled to a biopsy device of a biopsy system and the two beaded drive surfaces are configured to guide the flexible beaded rod through the flexible beaded rod aperture located in the distal face.

Example 22

The marker delivery device of Example 21, wherein the flexible push rod is configured to be manually translated between the first gear and the second gear to deploy a marker.

Example 23

The marker delivery device of Example 21, further comprising a first spring coupled between the first gear and the housing, wherein first spring is configured to transition from a biased position to an unbiased position and configured to rotate the first gear; and a release mechanism removably coupled to the first gear.

Example 24

The marker delivery device of Example 23, further comprising a second spring coupled between the second gear and the housing, wherein second spring is configured to transition from a biased position to an unbiased position and configured to rotate the second gear when release mechanism uncouples from the first gear.

Example 25

The marker delivery device of Example 21, further comprising a coupling shaft configured to rotatably couple to a drive shaft from a biopsy device; and a gear assembly including a pair of bevel gears, wherein the gear assembly is in communication with the coupling shaft at a distal end and configured to rotatably drive the first gear.

Example 26

The marker delivery device of any one or more of the Examples 21 through 25, wherein the deployer tip includes a marker; a distal tip configured to engage a proximal face of a biopsy needle; a ramp configured to transversely engage the marker and translate the marker when the distal tip engages a proximal face of biopsy needle; a flap having a free end and a hinged end, wherein the hinged end is biased to hold marker within the deployer tip, and the free end is free to rotate in an arcuate path when marker engages ramp; a recess, wherein the recess slidably couples around the flexible push rod.

Example 27

The marker delivery device of any one or more of Examples 21 through 26 wherein the deployer tip includes a marker; a first living hinge constructed of a resilient material, wherein the first living hinge defines a plurality of arcuate half bores, wherein the first living hinge has a resting position and a flexed position; a flat portion proximal to living hinge and configured to hold a marker; and a distal tip configured to engage a proximal face of a needle to transition the living hinge from the resting position to the flexed position.

Example 28

The marker delivery device of Example 27 wherein deployer tip includes a second living hinge, wherein the first living hinge is located proximate to the flat portion, and the second living hinge is located distally to the flat portion and proximal to the distal tip.

Example 29

A biopsy system comprising: a biopsy device including a drive shaft having a first shaft adapter, a cannula having a lateral aperture, wherein the cannula is configured to remove tissue from the body through the lateral aperture, and a first latching feature; and a marker delivery device including a second shaft adapter configured to rotatably coupled to the first shaft adapter, an annular ring having a second latching feature removably couples to first latching feature, a flexible push rod configured to translate through the cannula to deploy a marker when actuated by the drive shaft of the biopsy device.

Example 30

A method of deploying a biopsy marker to a biopsy site, comprising: translating a flexible push rod having a deployer tip through a biopsy needle to a lateral aperture of the biopsy needle; engaging a proximal face of the biopsy needle with a distal tip of the deployer tip; compressing a living hinge by translating the flexible push rod against the proximal face of the biopsy needle; and deploying the marker laterally through the lateral aperture of the biopsy needle.

Example 31

The method of Example 30, further comprising storing the flexible push rod on a stowage drum; releasing a spring tension, rotating the stowage drum with a spring; meshing a first engagement surface feature on the stowage drum with a second engagement surface on the flexible push rod; and deploying the marker through the cannula with a coordinated linear and rotational motion of flexible push rod.

Example 32

The method of Example 31, further comprising supporting the flexible push rod with one or more gears; and guiding the flexible push rod into the proximal end of cannula.

Example 33

A method of deploying a biopsy marker to a biopsy site, comprising: coupling a marker delivery device to a proximal end of a biopsy device with a latching feature and coupling a shaft adapter of the marker delivery device to a drive shaft of the biopsy device; actuating a motor within the biopsy device to rotate the shaft adaptor and thereby rotate a drive wheel of the marker delivery device; and engaging a flexible push rod of the marker delivery device with the drive wheel to translate the flexible push rod to deploy a marker from the marker delivery device.

V. CONCLUSION

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art.

For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

I claim:

1. A marker delivery device comprising:
   (a) a housing;
   (b) a flexible push rod, the flexible push rod including a first transverse drive surface and a deployer tip, the deployer tip being configured to receive a biopsy site maker;
   (c) a first wheel having a second transverse drive surface, the first transverse drive surface being configured to be driven by the second transverse drive surface to translate the flexible push rod distally; and
   (d) a spring in communication with the first wheel, the spring including a helical or spiral portion centered around the rotational axis of the first wheel, the spring further including a first end and a second end, the first end being coupled to one or more components in a fixed position relative to the first wheel, the second end being coupled to the first wheel, and the spring further having a resilient bias configured to rotate the first wheel and thereby translate the flexible push rod in a coordinated linear and rotational movement through a cannula to deploy the marker.

2. The marker deliver device of claim 1, the deployer tip including a flap having a free end and a hinged end, the flap being configured to transition between an open state and a closed state, the hinged end being configured to be held in the closed state by an interior surface of a biopsy needle, the free end being further configured to rotate in an arcuate path to transition the flap to the open state when not held closed by the interior surface of the biopsy needle, the deployer tip further including a distal tip, a ramp, and a recess, the distal tip being configured to engage a proximal face of the biopsy needle, the ramp being configured to transversely engage the marker and translate the marker in a transverse direction relative to the biopsy needle when the distal tip engages the proximal face of the biopsy needle, the recess being slidably coupled to the flexible push rod, the recess being configured to permit the flexible push rod to translate through the recess to engage the marker and translate the marker along the ramp.

3. The marker delivery device of claim 1, the flexible push rod including a smooth side, the smooth side being configured to slidably engage an inner surface of a biopsy needle.

4. The marker delivery device of claim 1, further comprising a sterile lubricant disposed within the housing, the sterile lubricant being configured to reduce friction between an interior surface of the housing and at least a portion of the flexible push rod.

5. The marker delivery device of claim 1, further comprising the first shaft, the first shaft being configured to rotatably couple the first wheel to the housing, the first end of the spring being coupled to the first shaft, the spring having a biased position and a relaxed position, the spring in the biased position being configured to be under tension, and the spring in the relaxed position being configured to rotate the first wheel and translate push rod in a coordinated linear and rotational movement through the cannula to deploy the marker.

6. The marker delivery device of claim 5, further comprising a release mechanism, the release mechanism being configured to removably couple to the first transverse drive surface, the release mechanism being further configured to hold the spring in the biased position and to release the tension in the spring to thereby transition the spring from the biased position to the relaxed position.

7. The marker delivery device of claim 5, further comprising a release mechanism, the release mechanism being configured to removably coupled to the second transverse drive surface, the release mechanism being further configured to hold the spring in the biased position and release the tension in the spring to thereby transition the spring from the biased position to the relaxed position.

8. The marker delivery device of claim 5, further comprising a second wheel having a third transverse drive surface, the third transverse drive surface being configured to engage the first transverse drive surface to support the flexible push rod in the transverse direction relative to the flexible push rod.

9. The marker delivery device of claim 8, further comprising a release mechanism, the release mechanism being configured to removably couple to the third transverse drive surface, the release mechanism being further configured to hold the spring in the biased position and release the tension in the spring to thereby transition the spring from the biased position to the relaxed position.

10. The marker delivery device of claim 8, further comprising a third wheel having a fourth transverse drive surface, the fourth transverse drive surface being configured to engage the third transverse drive surface to hold the second wheel stationary while the spring is in the biased position.

11. The marker delivery device of claim 10, the first transverse drive surface, the second transverse drive surface, the third transverse drive surface, and the fourth transverse drive surface all including a beaded portion.

12. The marker delivery device of claim 10, further comprising a release mechanism, the release mechanism being configured to removably couple to the fourth drive surface, the release mechanism being further configured to hold the spring in the biased position and to release the tension in the spring to thereby transition the spring from the biased position to the relaxed position.

13. The marker delivery device of claim 12, the first transverse drive surface, the second transverse drive surface, the third transverse drive surface, and the fourth transverse drive surface all including a plurality of gear teeth.

14. The marker deliver device of claim 1, the deployer tip including a first living hinge, a flat portion, and a distal tip, the first living hinge including a resilient material and defining a plurality of arcuate half bores, the first living hinge being configured to transition between a resting position and a flexed position, the flat portion being disposed proximally of the first living hinge and being configured to hold the marker, the distal tip being configured to engage a proximal face of a biopsy needle to thereby transition the first living hinge from the resting position to the flexed position.

15. The marker delivery device of claim 14, the deployer tip further including a second living hinge, the first living hinge being disposed proximally relative to the flat portion, the second living hinge being disposed distally relative to the flat portion, the second living hinge being further disposed proximally relative to the distal tip.

16. A marker delivery device comprising:
(a) a housing;
(b) a flexible push rod, the flexible push rod including a first transverse drive surface and a deployer tip, the deployer tip being configured to receive a biopsy site maker;
(c) a first wheel having a second transverse drive surface, the first transverse drive surface being configured to be driven by the second transverse drive surface to translate the flexible push rod distally; and
(d) the deployer tip of the flexible push rod including a distal tip, a flat portion, an arcuate portion, and a living hinge including a resilient material, the living hinge being configured to transition between a resting and flexed position upon sufficient pressure to force the flat portion and arcuate portion to flex from engagement of the distal tip with the proximal face of a biopsy needle, wherein the living hinge defines a plurality of arcuate half bores.

17. The marker delivery device of claim 16, wherein the flat portion is disposed proximal to the living hinge and configured to hold the marker.

18. A marker delivery device comprising:
(a) a housing;
(b) a flexible push rod, the flexible push rod including a first transverse drive surface and a deployer tip, the deployer tip being configured to receive a biopsy site maker;
(c) a first wheel having a second transverse drive surface, the first transverse drive surface being configured to be driven by the second transverse drive surface to translate the flexible push rod distally;
(d) a spiral spring including a helical or spiral portion wrapped around the rotational axis of the first wheel and a spring end joined to the first wheel, the spring further having a resilient bias configured to rotate the first wheel and thereby translate the push rod; and
(e) the deployer tip including a living hinge defining a plurality of arcuate half bores, the living hinge being configured to translate between a resting and flexed position upon translation of the push rod.

19. The marker delivery device of claim 18, wherein the living hinge including a resilient material.

\* \* \* \* \*